United States Patent
Bishop et al.

(10) Patent No.: US 12,223,092 B2
(45) Date of Patent: Feb. 11, 2025

(54) MODIFYING DATA FROM A SURGICAL ROBOTIC SYSTEM

(71) Applicant: CMR SURGICAL LIMITED, Cambridge (GB)

(72) Inventors: Steven Bishop, Cambridge (GB); Stephen Bell, Cambridge (GB); Ricardo Michael Henderson Da Silva, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 330 days.

(21) Appl. No.: 17/626,312

(22) PCT Filed: Jul. 10, 2020

(86) PCT No.: PCT/GB2020/051677
§ 371 (c)(1),
(2) Date: Jan. 11, 2022

(87) PCT Pub. No.: WO2021/005380
PCT Pub. Date: Jan. 14, 2021

(65) Prior Publication Data
US 2022/0286687 A1  Sep. 8, 2022

(30) Foreign Application Priority Data

Jul. 11, 2019 (GB) .................................... 1909992
Feb. 20, 2020 (GB) .................................... 2002390

(51) Int. Cl.
*G06F 21/62* (2013.01)
*A61B 34/35* (2016.01)
(Continued)

(52) U.S. Cl.
CPC .......... *G06F 21/6254* (2013.01); *A61B 34/35* (2016.02); *A61B 34/37* (2016.02);
(Continued)

(58) Field of Classification Search
CPC ................. G06F 21/6254; A61B 34/37; A61B 2034/301; A61B 34/35; G16H 30/40; G16H 40/67; H04N 19/136
See application file for complete search history.

(56) References Cited

U.S. PATENT DOCUMENTS 8,462,681 B2  6/2013 Pochiraju et al.
11,069,036 B1  7/2021 Simhadri et al.
(Continued)

FOREIGN PATENT DOCUMENTS

CN  106999257 A  8/2017
CN  107615395 A  1/2018
(Continued)

OTHER PUBLICATIONS

Japanese Notification of Reason for Rejection from corresponding Japanese Application No. 2022-500999 dated Feb. 21, 2023.
(Continued)

*Primary Examiner* — Kira Nguyen
(74) *Attorney, Agent, or Firm* — Lando & Anastasi, LLP

(57) ABSTRACT

A method of reducing a data volume of a data stream in a surgical robotic system, the surgical robotic system comprising a robot having a base and an arm extending from the base to an attachment for an instrument, the arm comprising a plurality of joints whereby the configuration of the arm can be altered, the method comprising: receiving a data stream captured by the surgical robotic system, the data stream comprising data relating to a surgical procedure and having a first data volume; identifying a feature in the received data stream indicative of an event in the surgical procedure; and modifying, in dependence on the identified feature, the received data stream to generate a modified data stream having a second data volume that is smaller than the first data volume.

19 Claims, 8 Drawing Sheets

(51) Int. Cl.
*A61B 34/37* (2016.01)
*G06N 20/00* (2019.01)
*G16H 20/40* (2018.01)
*G16H 30/40* (2018.01)
*G16H 40/67* (2018.01)
*H04L 9/40* (2022.01)
*H04N 19/136* (2014.01)
*A61B 34/30* (2016.01)

(52) U.S. Cl.
CPC ............. *G06N 20/00* (2019.01); *G16H 20/40* (2018.01); *G16H 30/40* (2018.01); *G16H 40/67* (2018.01); *H04L 63/0421* (2013.01); *H04N 19/136* (2014.11); *A61B 2034/301* (2016.02)

(56) References Cited

U.S. PATENT DOCUMENTS

| | | | |
|---|---|---|---|
| 11,132,462 | B2 | 9/2021 | Shelton, IV et al. |
| 2012/0177256 | A1 | 7/2012 | Keefe et al. |
| 2012/0307027 | A1 | 12/2012 | Popovic et al. |
| 2014/0051921 | A1* | 2/2014 | Miller ................ H04N 21/2662 600/109 |
| 2014/0188514 | A1* | 7/2014 | Balignasay ............ G16H 10/60 705/3 |
| 2014/0287393 | A1 | 9/2014 | Kumar et al. |
| 2015/0134365 | A1 | 5/2015 | Keefe et al. |
| 2015/0256790 | A1 | 9/2015 | Priest |
| 2017/0249432 | A1* | 8/2017 | Grantcharov ............ G06F 1/12 |
| 2017/0255751 | A1 | 9/2017 | Sanmugalingham |
| 2018/0122506 | A1 | 5/2018 | Grantcharov et al. |
| 2018/0271615 | A1 | 9/2018 | Mahadik et al. |
| 2019/0183591 | A1* | 6/2019 | Johnson ................ B25J 9/1666 |
| 2019/0201136 | A1 | 7/2019 | Shelton, IV et al. |
| 2019/0205441 | A1 | 7/2019 | Shelton, IV et al. |
| 2019/0205566 | A1* | 7/2019 | Shelton, IV ........... G16H 40/20 |
| 2019/0206562 | A1 | 7/2019 | Shelton, IV et al. |
| 2020/0107891 | A1 | 4/2020 | Ohashi et al. |
| 2020/0222133 | A1* | 7/2020 | Shuma .................... H04L 67/10 |
| 2020/0372180 | A1* | 11/2020 | Venkataraman ..... A61B 90/361 |
| 2021/0012032 | A1 | 1/2021 | Bishop et al. |

FOREIGN PATENT DOCUMENTS

| | | |
|---|---|---|
| CN | 109063506 A | 12/2018 |
| EP | 3505042 A1 | 7/2019 |
| EP | 3506299 A1 | 7/2019 |
| JP | 2005135344 A | 5/2005 |
| JP | 2014166298 A | 9/2014 |
| JP | 2015532040 A | 11/2015 |
| JP | 2018047088 A | 3/2018 |
| KR | 10-2019-0000107 A | 1/2019 |
| RU | 2412799 C2 | 2/2011 |
| RU | 2412800 C2 | 2/2011 |
| RU | 2601199 C2 | 10/2016 |
| RU | 2662883 C2 | 7/2018 |
| RU | 2672524 C2 | 11/2018 |
| WO | 2016044920 A1 | 3/2016 |
| WO | 2016149794 A1 | 9/2016 |
| WO | 2019133059 A1 | 7/2019 |
| WO | 2021005380 A1 | 1/2021 |
| WO | 2021005381 A1 | 1/2021 |
| WO | 2023278965 A1 | 1/2023 |

OTHER PUBLICATIONS

Russian Office Action from corresponding Russian Application No. 2022103245 dated Jan. 24, 2024.
Russian Search Report from corresponding Russian Application No. 2022103245 dated Jan. 23, 2024.
Japanese Notification of Reason for Rejection from corresponding Japanese Application No. 2022-500997 dated Aug. 22, 2023.
Japanese Notification of Reason for Rejection from corresponding Japanese Application No. 2022-500997 dated Feb. 3, 2023.
Australian Examination Report No. 1 from corresponding Australian Application No. 2020311031 dated Feb. 24, 2023.
Münzer B. et al., "Domain-Specific Video Compression for Long-term Archiving of Endoscopic Surgery Videos," 2016 IEEE 29th International Symposium on Computer-Based Medical Systems, pp. 312-317.
Monteiro et al., "A machine learning methodology for medical imaging anonymization" 25-29 Agosto 2015 2015 37th Annual International Conference of the IEEE Engineering in Medicine and Biology Society (EMBC) DOI: 10.1109/EMBC.2015.7318626 https://ieeexplore.ieee.org/abstract/document/7318626.
Indian Examination Report from corresponding Indian Application No. 202227007050 dated Jun. 29, 2022.
Russian Office Action from corresponding Russian Application No. 2022103251 dated Mar. 27, 2024.
Russian Search Report from corresponding Russian Application No. 2022103251 dated Mar. 26, 2024.
Australian Examination Report No. 2 from corresponding Australian Application No. 2020311031 dated Aug. 21, 2023.
Chilean First Office Action from corresponding Chilean Application No. 202200076 dated Jul. 13, 2023.
Chilean First Office Action from corresponding Chilean Application No. 202200077 dated Jul. 13, 2023.
Cummins, J. et al. "Steganography and Digital Watermarking," School of Computer Science, The University of Birmingham, Copyright 2004, Version 1.2, pp. 1-23.
Notification of Transmittal of the International Search Report and the Written Opinion of the International Searching Authority from corresponding PCT/GB2020/051677 dated Oct. 2, 2020.
Notification of Transmittal of the International Search Report and the Written Opinion of the International Searching Authority from corresponding PCT/GB2020/051678 dated Sep. 15, 2020.
United Kingdom Examination Opinion from corresponding United Kingdom Application No. GB2002390.9 dated Jul. 31, 2020.
United Kingdom Search Report from corresponding United Kingdom Application No. GB1909992.8 dated Dec. 11, 2019.
United Kingdom Examination Report from corresponding United Kingdom Application No. GB1909992.8 dated Sep. 1, 2022.
Australian Examination Report No. 1 from corresponding Australian Application No. 2020309810 dated Mar. 6, 2023.
Eadie, L. et al., "Telemedicine in surgery", British Journl of Surgery 2003, 90: 647-658.
Loukas, C., "Video content analysis of surgical procedures", Surgical Endoscopy, Oct. 26, 2017, 32: 553-568.
Australian Examination Report No. 2 from corresponding Australian Application No. 2020309810 dated Aug. 2, 2023.
Indian Hearing Notice from corresponding Indian Application No. 202227007048 dated Oct. 9, 2024.
United Kingdom Examination Report from corresponding United Kingdom Application No. GB2002390.9 dated Nov. 2, 2023.

* cited by examiner

MODIFYING DATA FROM A SURGICAL ROBOTIC SYSTEM

CROSS-REFERENCE TO RELATED APPLICATIONS

This application is a U.S. National Phase Application under 35 U.S.C. § 371 of International Application No. PCT/GB2020/051677, filed Jul. 10, 2020, which claims priority to United Kingdom Application No. 2002390.9, filed Feb. 20, 2020 and United Kingdom Application No. 1909992.8, filed Jul. 11, 2019. Each application referenced above is hereby incorporated herein by reference in its entirety for all purposes.

FIELD OF THE INVENTION

This invention relates to modifying data from a surgical robotic system for reducing a data volume of a data stream in a surgical robotic system.

BACKGROUND

It is known to use robots for assisting and performing surgery. FIG. 1 illustrates a typical surgical robot 100 which consists of a base 108 and an arm 102. An instrument 105 is coupled to the arm. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. As illustrated, at its distal end, the instrument comprises an end effector 106 for engaging in a medical procedure. The term 'instrument' encompasses an endoscope for imaging a surgical site.

The surgical robot 100 is controlled remotely by an operator (e.g. surgeon) via an operator console 200 shown in FIG. 2. The operator console 200 may be located in the same room (e.g. operating theatre) as the surgical robot 100 or remotely from it. The operator console 200 comprises input devices 202, 204 for controlling the state of the arm 102 and/or the instrument 105 attached thereto. The input devices 202, 204 may be handgrips or hand controllers mounted on parallelogram linkages. A control system converts the movement of the hand controllers into control signals to move the arms, joints and/or instrument end effector of a surgical robot. The operator console 200 also comprises a display 206. The display 206 is arranged to be visible to a user operating the input devices 202, 204. The display is used to display a video stream of the surgical site (e.g. endoscope video).

Some surgical procedures may require several surgical robots, each one carrying an instrument or other implement which is used concurrently with the others at the surgical site. FIG. 3 illustrates a surgical robotic system 300 with multiple robots 302, 304, 306 operating in a common workspace on a patient 308. For example, surgical robots are often used in endoscopic surgery (e.g. laparoscopic surgery), which also may be referred to as minimally invasive surgery. As is known to those of skill in the art, during an endoscopic procedure the surgeon inserts an endoscope through a small incision or natural opening in the body, such as, but not limited to, the mouth or nostrils. An endoscope is a rigid or flexible tube with a camera attached thereto that transmits real-time images to a video monitor (e.g. display 206) that the surgeon uses to help guide their tools through the same incision/opening or through a different incision/opening. The endoscope allows the surgeon to view the relevant area of the body in detail without having to cut open and expose the relevant area. This technique allows the surgeon to see inside the patient's body and operate through a much smaller incision than would otherwise be required for traditional open surgery. Accordingly, in a typical robotic endoscopic surgery there is an endoscope attached to one surgical robot arm and one or more other surgical instruments, such as a pair of graspers and/or a scissors, attached to one or more other surgical robot arms.

FIG. 4 illustrates an example endoscope 400 which is attachable to the end of a robot arm for use in minimally invasive surgery. The endoscope 400 has a distal end 402 for insertion into the surgical site of the patient, and a proximal end 404. The distal end 402 is connected to the proximal end 404 by an elongate shaft 406. The proximal end 404 comprises an interface 408 for engaging the end of the robot arm. The endoscope 400 has a power source and a light source for illuminating the surgical site. The endoscope 400 also has a data line for extracting the image data from the surgical site. These may all be attached to the proximal end 404 of the endoscope 400 independently and externally of the robot arm, as shown in FIG. 4. In FIG. 4, power is applied through stem 412, image data is extracted through stem 412, and light is applied through light stem 410. In an alternative implementation, any one or more of the light input, power input and data output may be applied/extracted to the endoscope through the robot arm. The endoscope 400 mounts to the end of the robot arm. The endoscope interface 408 engages a complementary interface of the robot arm. The endoscope 400 is attachable to and detachable from the robot arm via the robot arm and endoscope interfaces. In some cases, the endoscope 400 is operable independently of the robot arm in its detached state. In other words, in these cases the endoscope 400 can be operated manually by a member of the operating room staff when detached from the robot arm.

In addition to the images captured by the endoscope (which may be collectively referred to herein as the endoscope video) being used during surgery, the images captured by the endoscope may be recorded and subsequently used for a variety of purposes such as, but not limited to, learning and/or teaching surgical procedures, and assessing and/or reviewing the performance of the surgeon (by a third party or by the surgeon themselves).

In addition to the endoscope video, telemetry from the robotic system, data relating to the state of the robotic system and audio in the operating room and/or adjacent a control console can be captured. Further, captured data can include patient vital signs and/or healthcare (e.g. medical history). Captured data can include operator data, such as the identity of the operator, how long the operator has been operating, the procedures undertaken, and so on. Captured data may include data captured from or in relation to the environment surrounding the robotic system and/or equipment coupled to the robotic system. Such captured data can be used separately or in combination to assist with reviewing a procedure for learning and/or teaching purposes. Such captured data can be stored locally, at least temporarily, and transferred remotely for later analysis. It would be useful to increase the efficiency of data storage and/or transfer.

SUMMARY

This summary is provided to introduce a selection of concepts that are further described below in the detailed description. This summary is not intended to identify key features or essential features of the claimed subject matter, nor is it intended to be used to limit the scope of the claimed subject matter.

According to an aspect of the present invention, there is provided a method of reducing a data volume of a data stream in a surgical robotic system, the surgical robotic system comprising a robot having a base and an arm extending from the base to an attachment for an instrument, the arm comprising a plurality of joints whereby the configuration of the arm can be altered, the method comprising:
receiving a data stream captured by the surgical robotic system, the data stream comprising data relating to a surgical procedure and having a first data volume;
identifying a feature in the received data stream indicative of an event in the surgical procedure; and
modifying, in dependence on the identified feature, the received data stream to generate a modified data stream having a second data volume that is smaller than the first data volume.

The method may comprise generating the modified data stream by modifying one or more of: a first data portion of the received data stream before the identified feature; and a second data portion of the received data stream after the identified feature. One or both of the first data portion and the second data portion may relate to predetermined time periods.

The method may comprise identifying a further feature in the received data stream indicative of a further event in the surgical procedure, and generating the modified data stream by modifying a third time period of the received data stream: between the identified feature and the identified further feature; or before the first of the identified feature and the identified further feature and after the second of the identified feature and the identified further feature.

Identifying the feature may comprise determining whether a rule of a set of rules is satisfied and identifying the feature where the rule is satisfied. The rule may be satisfied where a parameter of a group of parameters of the surgical robotic system and/or the surgical procedure matches a predefined criterion. The received data stream may comprise the parameter. The parameter may be determined from analysis of the received data stream. The method may comprise saving and/or transferring the modified data stream.

The received data stream may comprise one or more data channel from a group of data channels comprising: video data received from an endoscope coupled to the surgical robotic system; audio data recorded in respect of the surgical procedure; telematics data corresponding to the surgical robotic system; state data comprising the state of at least a portion of the surgical robotic system; and further data transmitted by additional devices on the local network; and in which the method may comprise identifying the feature in dependence on one or more data channel from the group of data channels. The method may comprise identifying the feature in dependence on a first data channel of the group of data channels, and generating the modified data stream may comprise modifying one or more of: the first data channel and a second data channel of the group of data channels.

The identified feature may be indicative of a value of or change in one or more of: an attachment state of an instrument; an operational state of an instrument attached to the arm; an operational state or operational mode of the robotic system; a configuration of the arm and/or of an instrument attached to the arm; and a control state of the control console. The identified feature may be indicative of one or more of: a feature detected in the video data; sensor data; and data reported by an externally connected system.

The method may comprise generating the modified data stream by modifying one or more of: a video definition of at least a portion of the video data; a number of video channels of at least a portion of the video data; a frame rate of at least a portion of the video data; a colour gamut of at least a portion of the video data; a representation of the state of the robotic system; an audio definition of at least a portion of the audio data; a number of data channels in the group of data channels. The method may comprise modifying the received data stream such that the modified data stream comprises one or more of: a portion of video data having a first resolution and a portion of video data having a second, lower, resolution; a portion of video data having a first number of channels and a portion of video data having a second, smaller, number of channels; a portion of video data having a first frame rate and a portion of video data having a second, lower, frame rate; a portion of video data having a first colour gamut and a portion of video data having a second, smaller, colour gamut; data relating to changes in state of the robotic system in place of data relating to the state of the robotic system at a plurality of points in time between which the state does not change; a wire frame model of a known shape in the video data in place of full video or graphics render data relating to that known shape; a description of a structure in the video data in place of full video data relating to that structure; and a description of an absolute location and/or a relative location, and a description of a speed and/or a trajectory of movement, in place of full video data or full telematics data. The description of the structure may comprise a description of one or more of an anatomical structure, an instrument, and an end effector.

The method may comprise generating the modified data stream by compressing at least a portion of the received data stream. The method may comprise generating the modified data stream by compressing at least a portion of one or more data channel from the group of data channels.

The method may comprise generating the modified data stream by downsampling at least a portion of the received data stream. The method may comprise generating the modified data stream as the surgical procedure is being performed.

The method may comprise: generating the modified data stream in real time or substantially real time; sending the modified data stream to a remote processor thereby enabling the remote processor to perform real time or substantially real time analysis of the modified data stream; and receiving from the remote processor in real time or substantially real time the result of the analysis for assisting an operator of the surgical robotic system.

According to another aspect of the present invention, there is provided a data volume modification system for a surgical robotic system for reducing a data volume of a data stream in the surgical robotic system, the surgical robotic system comprising a robot having a base and an arm extending from the base to an attachment for an instrument, the arm comprising a plurality of joints whereby the configuration of the arm can be altered, the system comprising:
a receiver configured to receive a data stream captured by the surgical robotic system, the data stream comprising data relating to a surgical procedure and having a first data volume;
a feature detector configured to identify a feature in the received data stream indicative of an event in the surgical procedure; and a data modifier configured to modify, in dependence on the identified feature, the received data stream to generate a modified data stream having a second data volume that is smaller than the first data volume.

According to another aspect of the present invention, there is provided a data volume modification system for a surgical robotic system configured to perform the method described herein.

According to another aspect of the present invention, there is provided a surgical robotic system comprising a robot having a base and an arm extending from the base to an attachment for an instrument, and a data volume modification system configured to perform the method described herein.

According to another aspect of the present invention there is provided a non-transitory computer readable storage medium having stored thereon computer readable instructions that, when executed at a computer system, cause the computer system to perform the method as described herein.

Any feature of any aspect above can be combined with any one or more other feature of any aspect above. Any method feature may be rewritten as an apparatus feature, and vice versa.

BRIEF DESCRIPTION OF THE DRAWINGS

The present invention will now be described by way of example with reference to the accompanying drawings.

In the drawings.

DETAILED DESCRIPTION

Figure 1:
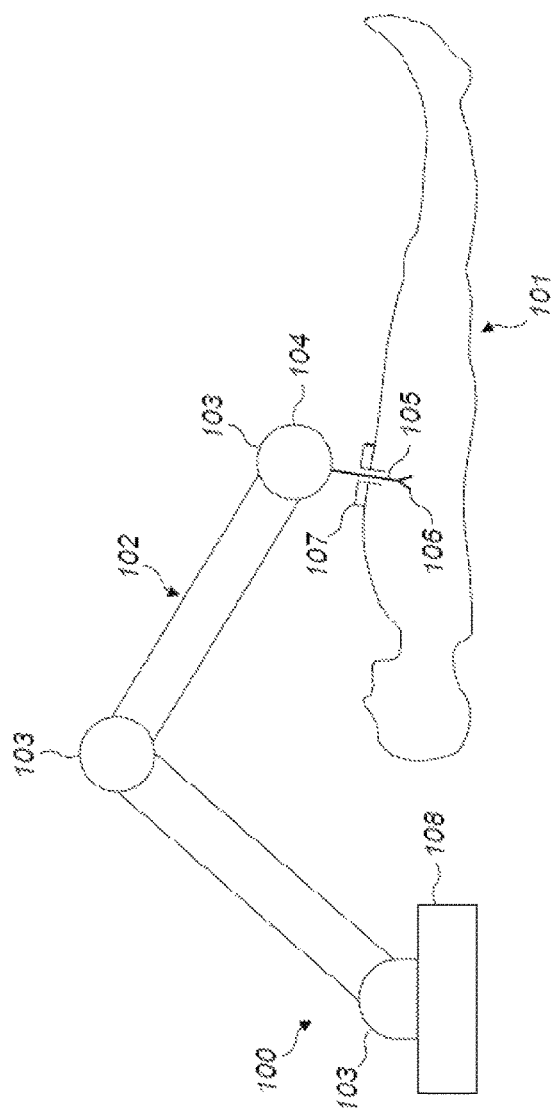
FIG. 1 schematically illustrates an example surgical robot performing an example surgical procedure.

The following description is presented by way of example to enable a person skilled in the art to make and use the invention. The present invention is not limited to the embodiments described herein and various modifications to the disclosed embodiments will be apparent to those skilled in the art. Embodiments are described by way of example only.

Data can be captured by a surgical robotic system. Such data can include setup data, tear down data, simulated training environment data, and data relating to the configuration of the system, such as the number, type and even individual part numbers and usage times of instruments coupled to the robot arms. The data can also include details of the hospital at which the procedure is being performed, details of the surgical team performing the procedure and details of the procedure itself. The data can include whether the system is left on overnight or 24 hours a day, 7 days a week, whether and when the system undergoes maintenance and the nature of that maintenance. Data captured by the surgical robotic system will include data relating to the procedure as it is performed, including one or more of video data captured by an endoscope used for viewing the surgical site, such as an internal surgical site inside a body cavity of a patient, audio data captured by the surgical robotic system, telematics data relating to the surgical robotic system, and state data relating to a state of the surgical robotic system. The state data can comprise data relating to the torque on or about a joint or plurality of joints, and/or accelerometer data relating to motion of all or a part of a robotic arm. The state data may comprise data relating to a system processor, such as CPU workload data and/or debugging outputs from a CPU.

The data captured by the surgical robotic system can enable robotic control over the robot arm of the surgical robotic system. For example, video captured by the endoscope is displayed on a screen that can be viewed by the surgeon, allowing the surgeon to effect appropriate control of the instruments coupled to the arms and of the arms themselves. The data can also be used for teaching and training purposes. The data can be passed to an additional console, for example for display, simultaneously with the data transferred to the surgeon's console, or at a later time, enabling a student to review the procedure, for example the actions taken by the surgeon during the procedure. The data may be stored locally for later transfer. The data may be transferred within the hospital to a data server. The data may be transferred off-site, i.e. out of the hospital's internal network. The data can enable review of the procedure internally at the hospital or externally by an external review board.

The amount of data captured by the surgical robotic system can be large enough that data bandwidth of a data link for transferring the data becomes a relevant consideration. Data storage size can also become a relevant consideration. Where saving and/or transferring the data, the present inventors have realised that it would be advantageous to reduce the data volume of the data in a way which does not affect the fidelity or quality of key aspects of the data. For example, whilst it is possible for the whole of the data to simply be downgraded in quality so as to reduce the data volume, but this would adversely affect the teaching and review processes which use that downgraded data. The present inventors have realised that it is desirable to selectively modify the data so as more efficiently to enable saving and transferring that data. Modifying the data in such a way can reduce the data size and bandwidth requirements.

Described herein are methods and apparatus for reducing a data volume of a data stream in a surgical robotic system. Data captured by the surgical robotic system, for example data generated and/or recorded by the system as the procedure is performed, can be received at a data volume modification system. The data volume modification system is suitably part of the surgical robotic system but might be separately provided. A feature detector of the data volume modification system is used to identify a feature in the received data stream which is indicative of an event in the surgical procedure, for example to determine that such an event has occurred, and the location or timing in the data that that event occurs. A data modifier is then used to generate a modified data stream using the received data stream and the identified feature. The modified data stream has a data volume that is smaller than the received data stream.

Figure 5:
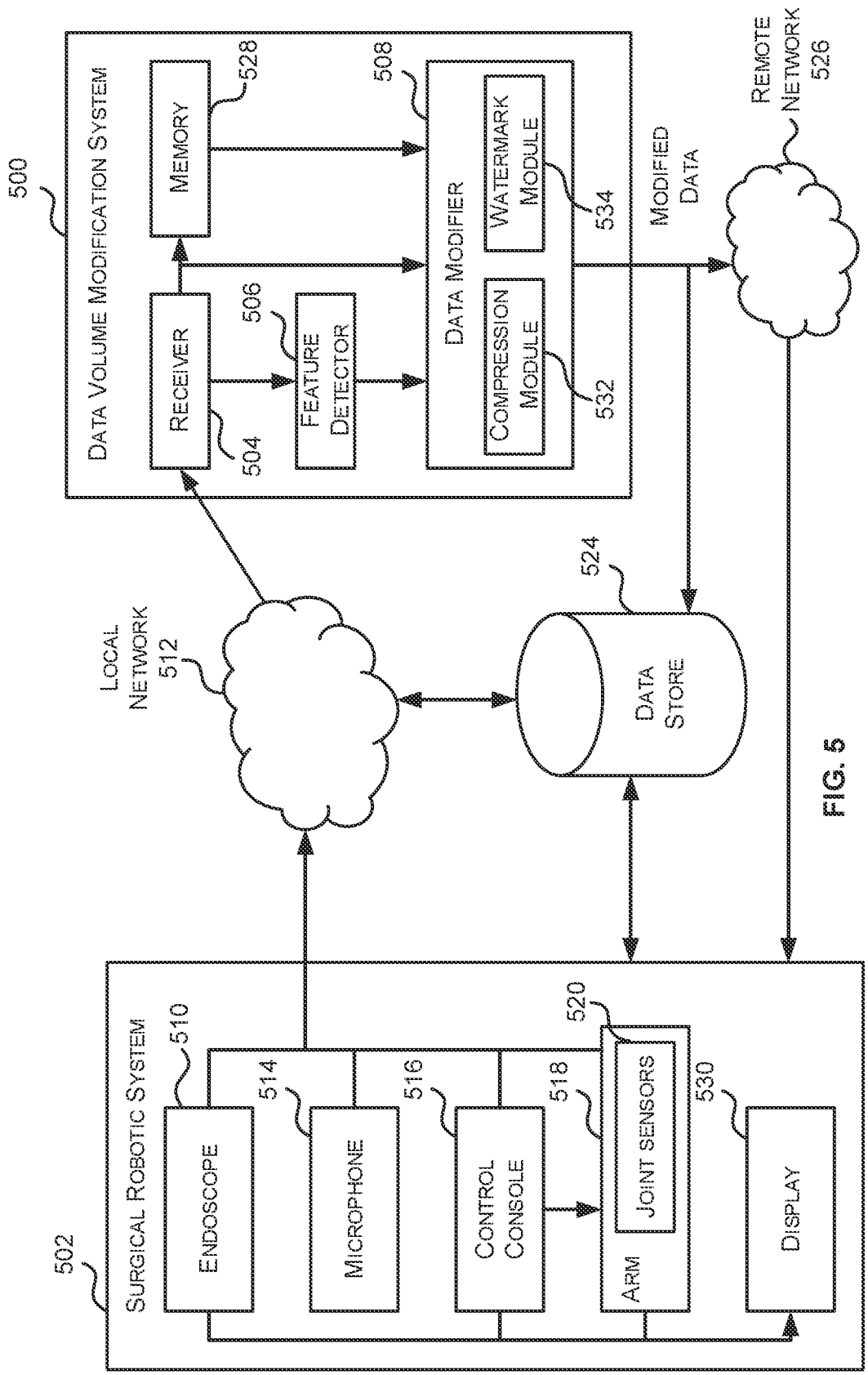
FIG. 5 is a block diagram of an example data volume modification system.

Reference is first made to FIG. 5, which illustrates an example data volume modification system 500 for automatically modifying data relating to a surgical procedure performed by a surgical robotic system 502. The surgical robotic system comprises at least one surgical robot having a base and an arm extending from the base to an attachment for an instrument. The arm comprises a plurality of joints whereby the configuration of the arm can be altered. An example surgical robotic system 502 is described below with reference to FIG. 6.

The data volume modification system 500 comprises a receiver 504, a feature detector 506 and a data volume modifier 508. One or more of the receiver 504, the feature detector 506 and the data volume modifier may be implemented by one or more computing-based devices, such as, but not limited to, the example computing-based device described herein with reference to FIG. 8. The receiver 504 is configured to receive a data stream comprising data relating to the surgical procedure. The receiver passes the received data stream to the feature detector 506 which is configured to identify a feature in the data stream. The data volume modifier 508 is configured to generate, in dependence on the identified feature and the data stream, a modified data stream having a data volume smaller than that of the received data stream. The generation of the modified data stream will be described in more detail below.

The data stream received by the receiver can comprise endoscopic video data, i.e. video or images captures by an endoscope 510. The receiver 504 is configured to receive the video data from the endoscope, for example via a local network 512. The local network can comprise one or more of an HDMI interface, an SDI interface, and other video interfaces. In some cases, the receiver can be configured to receive the video data from the endoscope via a direct coupling, which may comprise one or more of an HDMI interface, an SDI interface, and other video interfaces. The local network 512 is suitably on the hospital premises. The local network can comprise a high capacity data network. The local network can have sufficient capacity to transfer data from the surgical robotic system without there being data throttling, for example due to bandwidth limitations. The video data is likely to include video or images of the operating room itself—captured by the endoscope before the endoscope tip is inserted through a port towards the surgical site. (The term 'port' can be considered to comprise a physical port and/or a virtual port—as described elsewhere herein.) The field of view of the endoscope whilst it is coupled to the arm can be well characterised and potentially controlled to avoid capturing sensitive data. On the other hand, the endoscope is likely to be operational, i.e. capturing video, whilst being manually held or mounted to the robot arm. Whilst manually held, the field of view is likely to include images or video that are not typically useful when reviewing the procedure or for teaching purposes. Thus, transferring and/or storing such images or video may waste storage space and/or data bandwidth.

The data stream can also comprise audio data captured by a microphone 514 which optionally forms part of the surgical robotic system 502. The microphone can be located at or adjacent the robot arm, and/or at or adjacent a control console 516 of the surgical robotic system. In this way, the microphone can capture audio from the surgical procedure, including from operating room staff assisting in the surgical procedure, and from an operator of the control console such as a surgeon. The receiver 504 is configured to receive the audio data from the microphone, for example via the local network 512. The audio data may comprise discussions in advance of the surgery which may not be relevant to the surgical procedure itself. Thus, the audio data can comprise data which may not be useful when reviewing the procedure or for teaching purposes. Transferring and/or storing such audio data may waste storage space and/or data bandwidth.

The data stream can also comprise telemetry/telematics data and/or state data. The state data can indicate the state of at least a portion of the surgical robotic system. The telematics data and/or state data can be produced by the control console 516 as it effects control of an arm 518 of the robot. The telematics data and/or state data can be produced by sensors on the arm itself such as joint sensors 520 of the arm which are configured to sense the configuration of each of the arm joints. Additional data can include data captured by further sensors, such as temperature sensors, current sensors (from which battery level can be derived) and/or accelerometers. The receiver 504 is configured to receive the telematics data and/or the state data from the surgical robotic system (e.g. from the control console and/or from the arm), for example via the local network 512. All or a portion of the telematics data and/or the state data may be generated by the surgical robotic system 502 itself (e.g. data relating to the position and/or movement of the surgical robot arm(s), instrument(s) attached thereto, and any hand controllers that control the movement of the robot arm(s)). Telematics data and/or state data from the surgical robotic system that are generated before the surgical procedure begins may not be relevant for teaching and/or training purposes. For example, data can be captured during a setup phase. This data might be relevant for an internal review of the procedure, but may be less relevant in teaching or training. Thus, transferring and/or storing all of the telematics data and/or state data may waste storage space and/or data bandwidth.

Data received by the receiver 504 may comprise further data transmitted by additional devices on the local network such as tablet computers, mobile telephones, and specialised medical devices. These or other devices may be configured to transmit data packets in which flags can be set so as to define or mark a particular event. For example, if a surgeon logs onto a control console using a mobile telephone, that mobile telephone can transmit a data packet to the system indicative of the logon event. The further data may comprise patient vital sign data (e.g. heart rate, respiratory rate), healthcare data (e.g. medical history), operator data, such as the identity of the operator, how long the operator has been operating in that session, the procedures undertaken, data captured from or in relation to the environment surrounding the robotic system and equipment coupled to the robotic system.

Each of the video data, the audio data, the telematics data, the state data, and the further data can be considered to be a separate data channel of the data relating to the procedure captured by the system. The data channels are suitably time-synchronised with one another. The data channels may be time-synchronised in any suitable manner that allows features or events of one data channel to be correlated to a particular time or period of time, and/or a particular feature or event in another data channel. For example, a plurality of the data channels may include, or be linked to, common timestamps or a common timeline.

The video data and/or the audio data can comprise multiple channel data. For example, the video data can comprise a 'right' channel and a 'left' channel, suitable for representing a 3D image. The audio data can comprise a 'right' channel and a 'left' channel, suitable for representing stereo sound. In some cases, more than two video and/or audio channels may be present.

It can be desirable to generate the modified data stream by reducing the data volume of one or more of the video data, the audio data, the telematics data, the state data, and the further data.

It is possible for a data volume of a particular channel to increase whilst still reducing an overall data volume.

This is described in more detail elsewhere.

Suitably generating the modified data stream comprises modifying one or more of the following.

- a video definition of at least a portion of the video data. For example a relatively higher definition (e.g. ultra-high definition) portion of video data can be modified to reduce the definition to a relatively lower definition (e.g. high definition or standard definition).
- a number of video channels of at least a portion of the video data. For example, 3D data can be modified to be 2D data by omitting one of two video channels.
- a number of imaging modalities of at least a portion of the video data. For example, in hyperspectral imaging, sets of image data can be captured at a plurality of ranges of wavelengths. One or more of such sets of image data can be omitted.
- a frame rate of at least a portion of the video data. The received data stream may comprise data at a relatively higher frame rate, such as 60 Hz. The modified data stream may be modified to comprise a portion of data at a relatively lower frame rate, such as 30 Hz.
- a number of frames in a sequence of image frames. A subset of images or frames can be captured from a video stream, and that subset of images or frames transferred in place of the video stream. For example a static image can be captured from a video stream and that static image transferred in place of the video stream. This can be useful where there is no, or little, variation in the image data in the video stream over time. The subset can comprise a small number of frames, in the order of 2 to 9 frames, preferably 2 or 3 frames, which can be captured periodically from the video stream. The frames can be consecutive, or non-sequential, for example frames 1, 2, 3 in a sequence or frames 1, 3, 5 in a sequence (other non-sequential groups of frames are possible). The subset can be captured once in a given time period. The time period can be 1 second, 5 seconds, 10 seconds, 15 seconds, 20 seconds, and so on. The remaining frames in the video stream can be discarded. (Where the frame rate is 60 Hz, capturing 3 frames every second results in the remaining 57 frames being discarded.) Suitably the subset of frames captured is sufficient to obtain rate of change information and positional information. Capturing non-sequential frames can help make the change between frames more apparent. The number of frames to be captured can depend on a feature or event. These examples can be considered as an alternative modification of a frame rate.
- a colour gamut of at least a portion of the video data. The modified data may be modified so as to reduce the colour palette or colour gamut of a portion of the data stream. For example, a colour video can be modified to be a black and white video.
- a representation of the state of the robotic system. Data relating to changes in state of the robotic system may be retained in place of data relating to the state of the robotic system at a plurality of points in time between which the state does not change.
- an audio definition of at least a portion of the audio data, for example by reducing the frequency range of the audio data;
- a number of data channels in the group of data channels, for example by omitting one or more of the data channels in the modified data.

The method can comprise modifying the received data stream such that the modified data stream comprises one or more of the following.

- A wire frame model of a known shape in the video data in place of full video or graphics render data relating to that known shape.
- A description of a structure in the video data in place of full video data relating to that structure. The description of the structure can comprise a description of one or more of an anatomical structure, an instrument, and an end effector.
- A description of an absolute location and/or a relative location, and a description of a speed and/or a trajectory of movement, in place of full video data or full telematics data.
- A down-sampled portion of the received data stream, such as down-sampled audio/video.
- A bandpass filtered portion of the received data stream.
- A decimated portion of the received data stream. For example every 10th data point in a series of data points can be discarded. A smaller proportion of the data points may be retained. In another example, 1 in 10 data points can be retained and the remaining 9 can be discarded.
- A quantised portion of the received data stream. Such approaches can include using discrete cosine transforms and wavelet transforms.

Data encoded using a second coding scheme in place of data encoded using a first coding scheme. The first coding scheme may be a video stream, and the second coding scheme may be a translation of coordinate systems and/or a description (e.g. in English) of surgical events, which might be based on standard surgical ontologies.

The data stream can be transmitted through or by the surgical robotic system, for example through or by a robot arm of the surgical robotic system. Thus, the data stream may be received at the data volume modification system from the arm of the robotic system. Suitably, the data stream comprises a data feed from the surgical robotic system, such as a data feed from the arm of the robotic system.

The receiver 504 may receive the data stream relating to the surgical procedure via any suitable means. For example, in some cases the surgical robotic system 502 may provide the data to the receiver 504 via a wireless or wired communication connection 512 such as, but not limited to, an Ethernet connection, Wi-Fi® connection, Bluetooth® connection, Near-Field Communication (NFC) connection, HDMI connection, SDI connection, other video interface connections or the like. In these examples, all or a portion of the data may be provided to the receiver 504 in real time (or in substantially real time) while the surgical procedure is being performed.

In other cases, the data relating to the procedure may be captured by another device (e.g. a computing-based device) during the procedure and stored in a storage device 524 (e.g. a memory) and subsequently provided to the receiver 504 via a communication connection 512 or via any other suitable means. In some cases, all or a portion of the data may be stored, at the location at which the procedure is performed (e.g. the operating theatre), on a portable storage medium, such as, but not limited to a USB (universal serial bus) memory stick or SD card, and physically transported to the location of the receiver 504 where it is coupled to the receiver 504 so that the receiver 504 can read the data from the portable storage medium.

The feature detector 506 is configured to identify in the data stream a feature that is indicative of an event in the surgical procedure. The event can comprise any desired aspect of the procedure such as the stage in the procedure or an action taken by the surgeon or another member of the operating room staff. The event can characterise whether the system is left on overnight or 24 hours a day, 7 days a week. The event can characterise whether and when the system undergoes maintenance and the nature of that maintenance.

E.g., the event can include identifying the start and/or end of a suturing procedure, a cauterising procedure, a grasping procedure, a cutting procedure, a procedure of moving end effectors of one or more instruments to a desired location at the surgical site, an insufflation procedure, and so on.

The event can include identifying an operational state of an instrument coupled to the system, and/or an operational state of the system. For example, the system may be in a mode of a group of modes. The group of modes can include a setup mode in which instruments may be attachable to the system, but operative control of the instruments by a surgeon may not be enabled in that mode. The group of modes can include a surgical mode in which instrument attached to the system can be operatively coupled to the surgeon's control console, permitting control of the instruments to be effected by the surgeon. Thus, the event can include identifying when the system enters and/or leaves a particular mode, such as the surgical mode. Where it is determined that the instrument is not in an operational state, e.g. the instrument is not being actively controlled by a surgeon and/or the instrument is not operatively connected to a control console, the corresponding data portion can be indicated to not be relevant to the procedure, and need not be retained in full. Such a determination can be made using telemetry data or from video image analysis.

The event can include identifying any other desired aspect or feature of the data stream. For example, as discussed in more detail elsewhere herein, the system may be configured to detect when a portion of an instrument, such as an end effector of that instrument, passes through a port towards or away from the surgical site. The system may be configured to detect when the endoscope is inserted through a port towards the surgical site or is withdrawn from a port away from the surgical site. Such detection can be based on aspects of the data stream, such as video data (e.g. from analysis of the video data such as colour or changes in colour of the video data, intensity/brightness or changes in intensity/brightness of the video data, tracking an object in the video data, tracking the change in an identified part of the video data—see elsewhere herein for additional details).

The identified feature can be indicative of a value of, or a change in, one or more of a configuration of the arm and/or of an instrument attached to the arm, and a control state of the control console. The identified feature can be indicative of one or more of a feature detected in the video data, sensor data (including torque data, accelerometer data, temperature data, battery voltage data and so on), and data reported by an externally connected system.

The feature can be identified in dependence on the detection of any one of or any combination of the events described herein.

The identified feature can indicate the start and/or end of the surgical procedure or of a particular aspect or stage of the surgical procedure. It is not necessary in all situations to save or transfer with full accuracy all data before the procedure starts or after the procedure ends. Thus, parts of the data stream other than when the procedure is being performed may be modified to reduce the data volume of the data stream. Such modification can be performed without losing data relating to the procedure itself. An event can indicate the start of the surgical procedure. For example, the event can comprise detecting that an endoscope has been inserted through a port towards an internal surgical site. Another event can indicate the end of the surgical procedure, for example the event can comprise detecting that the endoscope has been removed from the port. It can be desirable to retain full data in respect of the procedure, e.g. the time period in between the two events, and the reduce the data volume of the data stream outside this time period.

In some cases, only a part of the procedure may be relevant. E.g., where the procedure includes an electrocautery step, and the data stream is being saved as part of electrocautery teaching materials, it is not necessary to save or transfer full details of other aspects of the procedure that do not relate to the electrocautery step. Thus, portions of the data stream not relating to the electrocautery step can be modified to reduce the associated data volume of those portions.

One approach to reducing the data volume of the data stream is to identify a portion or portions of the data stream for which it is desirable to retain full data quality, and to modify other portions of the data stream to reduce the data volume of those other portions. Another approach is to identify a portion or portions of the data stream for which it is not necessary to retain full data quality and to modify those identified portions to reduce the data volume of those portions.

To take an example, consider endoscope video. As the endoscope is attached to the robot arm, and before it is inserted through the port, it will capture video of the operating room (i.e. video from outside the surgical field). This video may comprise data that is of lower relevance for review or training. Once the endoscope is inserted through the port, it will capture video of the internal surgical site (i.e. video from inside the surgical field), which is more likely to relate to data that it is desirable to retain for review or training, i.e. such data is likely to be of higher relevance. This will remain the case until the endoscope is retracted from the port (when the video will transition from being inside the surgical field to being outside the surgical field), when it will again begin to capture video of the operating room, with the data then again being of lower relevance. The 'relevant' data can therefore comprise video captured between insertion of the endoscope through the port and retraction of the endoscope from the port, i.e. video of a target operative field, and suitably nothing else. This approach can thus involve determining when the endoscope is inserted through the port and when it is retracted from the port and retaining in full the data stream of any portion of video data captured between these identified times, i.e. when the endoscope is inserted through the port. Data in the data stream at other time (i.e. when the endoscope is not inserted through the port) can be removed or otherwise modified so as to reduce the data volume of the data stream.

A combination of the first and second approaches can be used.

In response to identifying the feature in the data stream, the feature detector 506 may be configured to generate an output indicating one or more of:

that the feature has been detected,
the type of feature detected, the time of the feature (i.e. the time that that feature occurred), the portion of the data stream to which the feature relates (such as part of a still or video image, or successive parts of a sequence of images, or more generally which of the data channels comprises the feature), and the duration of the feature.

The output is provided to the data modifier 508.

The data modifier is configured to receive the output from the feature detector and to receive the data stream via any suitable means, for example from the receiver. The data modifier could also be configured to receive the data stream over the local network 512. The data modifier is configured to generate a modified data stream based on the received data stream and the identified feature. The modified data can be saved to local or remote storage, such as to the storage device 524. The modified data can be transmitted over a remote network 526 such as the internet. The modified data can be transmitted by any suitable method, such as over a wired link or over a wireless connection to a local access point that connects to the remote network.

The data volume modification system 500 may be remote from the surgical robotic system 502. For example, the surgical robotic system 502 may be located in an operating theatre and the data volume modification system 500 may be in another room in the hospital or treatment centre. In other cases, the data volume modification system can be integrated with the surgical robotic system, for example at the control console.

Suitably the data volume modification system 500 is configured to process the data stream in real time (or in substantially real time). The data volume modification system can comprise a memory 528 e.g. a buffer memory for temporarily storing the received data stream. The data modifier 508 can read the stored data stream from the memory 528. Processing the data stream in (substantially) real time enables the modified data to be transmitted over the remote network, also in real time (or in substantially real time). The modified data can be transmitted to a server located in the cloud, e.g. to an assistance module at the server. The assistance module can analyse the modified data to extract performance or other metrics and/or to generate advice or suggestions in response to the analysis. The advice can comprise advice relating to the next step to take in a particular procedure, how to most effectively perform a given step, suggestions relating to the procedure being performed or the step in the procedure being performed, etc. This advice can be provided by the remote server, over the remote network 526, to the surgical robotic system 502, e.g. to a display 530. In this way, a surgeon operating the surgical robotic system can receive the advice/suggestions in (substantially) real time as they are performing the procedure on a patient.

In this way the data volume modification system enables use of a remotely-based assistance module to enhance the procedure as it is being performed by the surgeon. In some cases, the modified data can be sent to a remotely-located person such as another surgeon. In this way, a more experienced surgeon can offer timely advice to a less experienced colleague without needing to be in the same location.

In some cases, the data stream, as received by the receiver, is presented to an operator (e.g. surgeon) of the surgical robotic system in real time, contemporaneously with generating the modified data stream. This can help avoid latency issues in the generation of the modified data from impacting the performance of the surgery.

Suitably the received data stream is modified before it is saved or transferred to a remote location, e.g. a location remote from the operating room (or hospital) at which the procedure is performed. The data stream can be modified before it is saved to local storage, such as the storage device 524. The storage device can store both the unmodified data stream and the modified data stream.

Suitably, the operator of the surgical robotic system such as a surgeon, or another member of staff at the hospital, is able to control whether or not the data or modified data is saved and/or transferred. Thus, the data volume modification system can present a user with an option to locally save the data stream. The data volume modification system can present a user with an option to save and/or transfer the modified data stream, either to a local or to a remote location. In this way a user such as the surgeon or another member of hospital staff has oversight of how the data or modified data is used.

The data volume modification system may comprise a compression module 532, configured to compress at least a portion of the data stream in generating the modified data stream. The compression module can be provided at or as part of the data modifier 508. The compression module can be configured to compress the received data (such as by compressing the video channel of the received data, optionally together with additional data of the received data) when the endoscope is not inserted through the port. The compression module can compress the data in any suitable manner, for example by using a conventional compression algorithm such as a lossy compression algorithm. The compressed data may therefore have a smaller data volume than the uncompressed data.

In some cases, different segments or chapters of the received data can be compressed with different levels of compression. For example, the data stream can be segmented based on one or more feature of the data stream (or more generally, information relating to the surgical procedure). In this way, the data stream can be segmented according to one or more of the configuration of the arm, the type of instrument attached and/or its operational state, the operational state of the robotic system, the stage in the procedure, the surgeon controlling the robot, and so on. Each stage, or a group of stages, of the procedure can be associated with a different compression level. This can enable reductions in data volume to differ between the stages.

The data volume modification system may comprise a watermark module 534, configured to add a 'watermark' to one or both of the received data stream and the modified data stream. The watermark module can be provided at or as part of the data modifier 508. The watermark can comprise a digital signature and/or fingerprint. The watermark may be added to the data in such a way that at least a portion of the watermark can be considered to be 'hidden', i.e. it is not necessarily apparent that a watermark (or the hidden portion of the watermark) has been added. This can reduce the risk of the watermark (or the hidden portion of the watermark) being deliberately removed by a third party. For example, the watermark module may be configured to apply the watermark by one or more of encoding the watermark in the least significant bits of data, encoding the watermark as part of carrying out a discrete cosine transformation in respect of the data (for example when compressing the data), encoding the watermark using wavelet transformation, encoding the watermark using spread spectrum techniques, encoding the watermark using frequency and/or temporal masking, and so on.

The watermark module may be configured to add the watermark when the data is modified. In other implementations, the watermark module can be configured to add a watermark to the modified data when it is to be transferred remotely, for example in a further modification process. Thus the watermark module need not be provided as part of the data volume modification system, but can be provided separately. For instance, the watermark module may have access to the modified data, such as by being coupled to the data store 524 at which the modified data is stored. When the modified data is to be sent remotely, the watermark module can be configured to add the watermark at that stage, prior to the transfer. Details relating to the intended recipient and/or intended use of the modified data can be included in the watermark.

The provision of the watermark module enables the data (e.g. the modified data transferred to a remote server) to be tracked and/or identified. For instance, the watermark can comprise an identification of one or more of the hospital at which the procedure was performed, the surgeon/surgical team who performed the procedure, the robotic system used to perform the procedure (which could be identified by a unique serial number of one or more of the control console, the robot arm(s) and the instrument(s)), the type of the procedure, the date/time at which the procedure was performed, the person responsible for authorising the release of the data, an expiry date of the released data, and so on. Any desirable metadata can be included in the watermark. The watermarked modified data can thereby be tracked back to the hospital at which the procedure was performed. Thus on review of the modified data, any conclusions or results of the review (which might be carried out without knowing the details contained in the watermark) can be fed back to the relevant hospital/surgical team.

The watermark can comprise an indication of the use for which the modified data has been released. For example, modified data for a particular procedure may be released for review of that procedure, but not authorised for teaching—which could for example be because that procedure remains experimental. The watermark module can be configured to add a watermark that indicates that the data can be used for review (perhaps for review by a selected recipient which can be an individual or a hospital), and details of the person/organisation to whom the data was released. Should that data later be found to be used by another individual, or for another use, the release channel and the original authorised use can be determined from the watermark. For these purposes it may be useful if such information is contained in a hidden portion of the watermark, so that it will not (or cannot) be deliberately removed.

In some cases, where the data stream is segmented, different watermarks can be applied to different segments or groups of segments. This can be done for several reasons, including because a different instrument was used (so the instrument ID in the watermark might be different), because a different surgeon performed that part of the procedure (so the surgeon ID in the watermark might be different), because a segment has been released for a different purpose to another segment (so the details relating to recipient/purpose of use and so on in the watermark might be different).

Where data is stored at the local data store 524 and/or a remote data store, such data can be retained for a given amount of time. Retention of data for a minimum amount of time may be needed to satisfy legal or regulatory requirements. Suitably the data is associated with a lifespan value, indicating the length of time for which the data will be retained, and/or an expiry date, indicating the date on which the data can be deleted. The system can be configured to automatically delete the data once the lifespan value or expiry date is reached. For example, a hospital may have a policy of retaining data from surgical robotic procedures for a certain number of days, say 7 days. The lifespan value can therefore be set at 7 days. Once 7 days have expired from the completion of the procedure, the data relating to that procedure can automatically be deleted from local and/or remote storage. Instead of automatically deleting the data, a user may receive a prompt to confirm deletion of the data.

In some cases, the data volume modification system can be configured to automatically modify data once the lifespan value or expiry date is reached. In this way, where the data stream is retained without being modified, it may be available for a period of time corresponding to the lifespan value (or until the expiry date). During this time the full data is available for review, for example locally within the hospital at which the procedure was carried out. Such review may be by the surgeon and/or surgical team who carried out the procedure. Suitably the lifespan value/expiry date can be selected so that the full data is retained for a duration long enough that a standard post-procedure review can be carried out on the full data. For example, where it is hospital policy to perform such a review within 7 days of the procedure, the lifespan value can be set at 7 days. The data can then be modified automatically at the end of this period of time, and the modified data stream may remain available for a longer period.

In some cases, the data stream may be associated with a first lifespan value (or first expiry date). This lifespan value can determine the length of time for which the full data remains available. At the end of this time period, the data may be modified by the data volume modification system. The modified data (and optionally the data stream) may be associated with a second lifespan value (or second expiry date, later than the first expiry date). This second lifespan value can determine the length of time for which the modified data remains available. For example, the first lifespan can be selected to be 3 days, and the second lifespan can be selected to be 14 days. In this example, the full data can be saved for 3 days following the procedure. During this time the full data may be reviewed. After 3 days the data is automatically modified. The modified data is retained for a further 14 days, after which it is automatically deleted. Other time periods can be chosen as desired. The second lifespan value (second expiry date) can indicate that the modified data is never to be automatically deleted. Instead of the data being automatically modified/deleted, a user may be prompted to modify and/or delete the data, at the relevant stage. Such prompting can ensure that an authorised person remains responsible for the management of the data.

The full data will typically be retained locally. In some cases the modified data may be retained locally. In some cases the modified data will be retained remotely. Following modification, the system can be configured to transfer the modified data to a remote store, and to delete the data from the local store. Thus, in such cases, the full data may be available locally for a predetermined period of time, following which the modified data may be available remotely for a further predetermined period of time.

In some cases, once a data stream has expired or reached the end of its lifespan, it may be modified automatically prior to deletion. In this way, any recovery of the deleted data would reveal the modified data rather than the received data stream. In some cases, the data stream or modified data stream may be watermarked (or further watermarked) prior to deletion. Suitably the watermark indicates that the data is to be deleted. Thus, if the deleted data is restored, it can be determined that that data was deliberately deleted. In some cases, a playback system for replaying the data can be configured to prevent the playback of data with a watermark indicating that that data was deleted (or was to be deleted).

Figure 2:
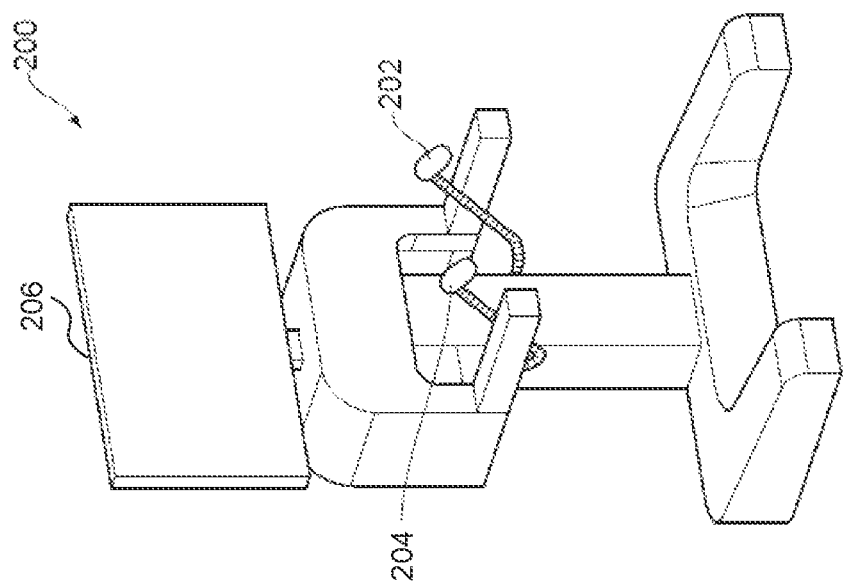
FIG. 2 schematically illustrates an example operator console.
Figure 3:
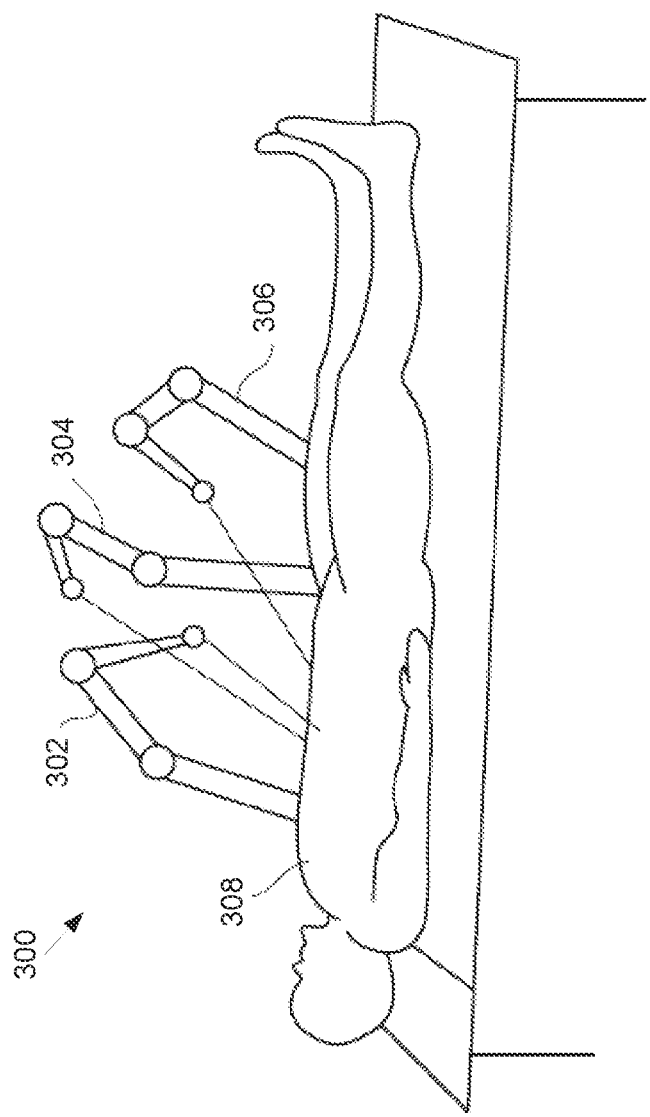
FIG. 3 schematically illustrates an example surgical robot system with a plurality of surgical robots.
Figure 6:
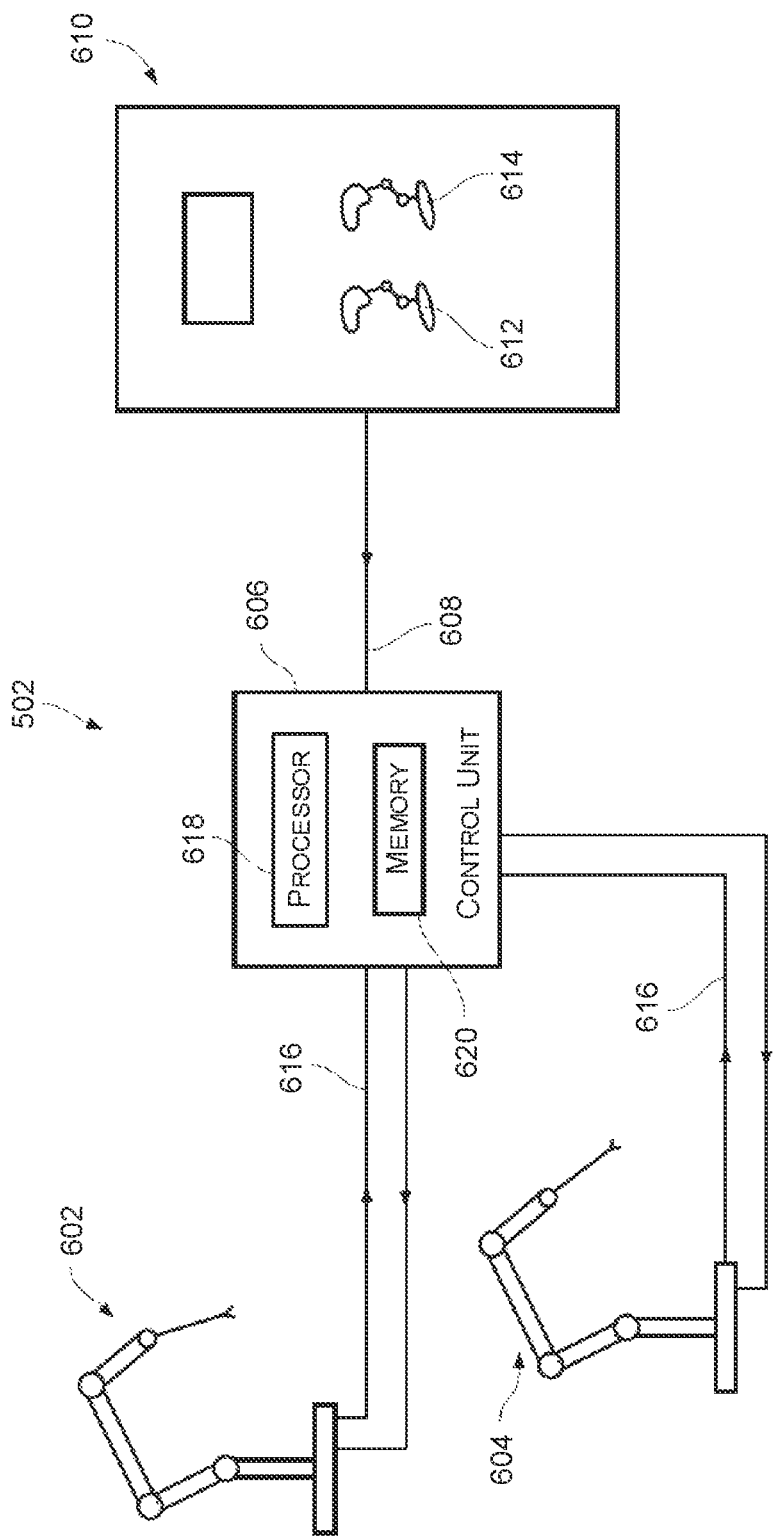
FIG. 6 schematically illustrates an example surgical robot system.

Reference is now made to FIG. 6 which illustrates an example surgical robotic system 502. In this example the surgical robotic system 502 comprises two surgical robots 602 and 604 driven by a control unit 606. The control unit 606 receives inputs 608 from an operator console 610 (such as, but not limited to the operator console 200 of FIG. 2), including inputs from first and second hand controllers 612, 614. The control unit 606 may receive other inputs from the operator console 610, such as foot pedal(s) inputs, voice recognition inputs, gesture recognition inputs, eye recognition inputs etc. The control unit 606 also receives inputs 616 from the surgical robots 602, 604. These inputs include sensor data from position sensors and torque sensors located on the robot arm joints. The control unit 606 may receive other inputs 616 from each robot, such as force feedback, data from or about the surgical instruments etc. The control unit 606 drives the robots 602, 604 in response to the inputs it receives from the robots 602, 604 and the operator console 610. The control unit 606 comprises one or more processors 618 and a memory 620. The memory 620 stores, in a non-transient way, software code that can be executed by the one or more processors 618 to control the drivers.

While the example surgical robotic system 502 of FIG. 6 comprises two surgical robots, it will be evident to a person of skill in the art that the methods and techniques described herein are equally applicable to surgical robotic systems with only one surgical robot and surgical robotic systems with more than two surgical robots.

The description above describes examples of identifiable events in a received data stream comprising a plurality of channels, the identification of which can lead to the data stream being modified. In such a case, a feature in a given data channel (for example the video data) can be identified and, in response, the data modifier can modify data in the same data channel (the video data). In some cases, one or more feature in one data channel can be identified and, in response, the data modifier can modify data in one or more other data channel as well as or instead of in the data channel in which the feature(s) was identified.

The identifiable event can comprise, or be determined in dependence on, a state of the surgical robotic system. The state of the surgical robotic system (i.e. state data comprising the state of at least a portion of the system) can comprise one or more of the attachment state of an instrument, the operational state of an instrument, the operational state of the robot, the configuration of the arm and/or of an instrument attached to the arm, and the control state of the control console.

Where an instrument such as an endoscope is not attached to the arm, it is likely that data in the data stream will not be relevant to the carrying out of the surgical procedure, since it is likely that the procedure will not have started at that point. Thus, the attachment state of the endoscope can be taken as a feature that indicates an event in the procedure—here, that the procedure itself is likely to have not started where the endoscope is not attached. Thus, identifying such a feature, in this example that the endoscope is not attached to the arm, means that the video data captured by the endoscope in this state can be marked or otherwise indicated to be modified by the data modifier to reduce the data volume of that portion of the video data, for example since it is likely to be of less relevance for review and/or teaching purposes. In this example, the feature (the attachment state of the endoscope) will be detected throughout the period in which the endoscope is unattached. The data stream may therefore be modified for the period in which the feature is identifiable, e.g. until the endoscope is attached to the arm.

The identifiable feature can comprise the attachment of the endoscope to the arm (i.e. the event of the attaching the endoscope, rather than a state in which the endoscope is/remains attached). Thus, in such cases, it need not be the case that the feature is always present for the data to be modified. In such cases, where the attachment of the endoscope to the arm is determined to occur, it will be known that the preceding data stream was captured whilst the endoscope was not attached to the arm. In response to the determination of such a feature, the data modifier can modify the data preceding the feature. Where an attachment event is preceded by a detachment event (i.e. the endoscope is detached from an arm before being reattached to the arm, or attached to another arm) both events can be identified as features, in response to which the data modifier can be configured to modify the data stream between the features (occurrence of the events). In this way the data modifier can modify the video data for periods in which the endoscope is not attached to an arm. The modified data stream will have a smaller data volume than the received data stream, since the modified portions will have smaller data volumes than the unmodified portions. This usefully enables a saving in data storage (where the modified data stream is saved in place of the unmodified data stream) and/or in data bandwidth requirements (where the modified data stream is transferred in place of the unmodified data stream).

The above case is an example of the data modifier modifying one data channel in response to identifying a feature in another data channel. Here, the feature is identified in the state data, and the video data is modified.

The operational state of an instrument can indicate whether a surgical tool is currently being controlled by a surgeon. For example, where a grasper tool is attached to the arm, the operational state of the tool can indicate whether the grasper tool is activated, i.e. is being moved/used by the surgeon. Since the tool will not be used by the surgeon unless they have a view of the surgical site, it can be determined that when at least one tool attached to an arm of the robot is under active control, that the endoscope will be capturing images of the surgical site and so will be located within a patient cavity. Thus, where a tool is in an operative state, such a feature can indicate that subsequent video data relates to the surgical procedure being undertaken, e.g. the data is of relevance for review and/or training, and should be retained in full. In response to the identification of such a feature, the data modifier can be configured to modify preceding data in the received data stream. That is, where a tool enters an operative state, it can be determined that data relating to a previous state (e.g. an inoperative state) is of less relevance and can therefore be marked to be modified to reduce its data volume without this affecting the data quality of data portions of the data stream relating to the procedure itself, or of greater likely importance for review and/or training purposes.

The operational state of the robot can be used to characterise or segment data in the data stream, for example by indicating whether or not an endoscope is inserted through a port. The operational state of the robot may comprise a mode of the robotic system, or of the control console. The robotic system can be initialised into, or put into, a 'port training' mode. In this mode, an instrument (which may be an endoscope or other type of instrument such as a grasper instrument) can be attached to the arm, and positioned partly within a port (the port can be a virtual port, i.e. need not be a physical port—this is discussed in more detail below). The arm can be moved by a user pushing on the arm to enable the system to determine the location of the port. In this way the system can establish a location of a virtual pivot point (VPP) about which an instrument is restricted to pivot when inserted through the port. The system can then be moved into an 'instrument adjust' mode in which the instrument can be further inserted through the port, towards a position in which surgical control of the instrument can begin. For example, where the instrument is an endoscope, the instrument can be inserted until the tip of the instrument (which can house the endoscope imaging device) is located adjacent a desired surgical site. In other cases, the instrument can be inserted until the end effector of that instrument is within the field of view of an endoscope located at the surgical site. The system can be moved between the instrument adjust mode and a 'surgical' mode in which control of the instruments can be effected by an operator (e.g. surgeon). The system can suitably also be moved between the surgical mode and an 'instrument change' mode in which an instrument can be removed and replaced. Where the system is in the surgical mode, it can be determined that the endoscope is inserted through a port. Thus, in some cases, the data stream can be indicated to be 'more relevant' (e.g. more likely to comprise data of relevance for review and/or training, amongst other uses) where the system is in the surgical mode. At other times (when the system is in other modes) the data captured may comprise non-surgical data such as a view of the operating room, which might also include a view of the patient. Accordingly, the data modifier can modify data captured before the surgical mode is entered and/or data captured after the system has exited the surgical mode.

As mentioned, the port can comprise a virtual port. In some cases the port comprises a physical port through which an instrument can pass. In some cases, the port can be a 'virtual port'—a physical port need not be present. This can be the case where, for example, an instrument is to be inserted through a patient orifice, such as the patient's nostril or mouth. The virtual port can be defined in a manner analogous to that described above. For example, an instrument such as an endoscope can be at least partly inserted through the virtual port (e.g. into a patient's nostril) and the arm moved by a user to enable the system to determine the location in space of the virtual port. In this way the system can establish a location of a virtual pivot point (VPP) about which an instrument is restricted to pivot when inserted through the virtual port.

In some cases, the state of the surgical robotic system can comprise the configuration of the arm and/or of an instrument attached to the arm. This can provide information on how the instrument/arm is positioned, from which it can be determined whether it is likely that, for example, a procedure is being performed and/or the endoscope is inserted into the patient cavity.

The state of the surgical robotic system can comprise whether or not the virtual pivot point (VPP) for an instrument such as the endoscope is set. The setting of the VPP can indicate that the instrument is inserted through the port. The system can determine whether or not an instrument is inserted through the port based on knowledge of the location of the VPP and the location of the end effector and instrument shaft of the instrument (e.g. from arm kinematics). The state of the surgical robotic system can comprise the position and/or movement of an instrument or of a portion of the instrument, for example whether the tip of the instrument is inside a patient cavity or whether the tip has passed through a port or the defined VPP associated with that port.

In some cases an external source can indicate a state of the system. For example, a port may comprise an instrument sensor configured to sense when an instrument, or a particular part of an instrument, passes through the port. The instrument sensor may comprise a magnetic sensor configured to magnetically sense the instrument. For example the instrument sensor may comprise a Hall effect sensor. The instrument may be at least partially magnetic or magnetised. The instrument tip may comprise a magnet for sensing by the Hall effect sensor.

It will be understood that there can exist different ways of determining the same thing, e.g. whether the endoscope tip is inserted within a patient cavity. The data modifier can be configured to modify the data stream in dependence on any one, or any combination of, identified features. In this way, the data volume modifier system can operate with a redundancy, to better ensure accuracy in which portion or portions of the received data stream are to be modified even where a system fault might cause one feature to be inaccurately determined or identified. This can assist in reducing the data volume of the modified data stream by helping to ensure that only those portions of the received data stream that are desired to be retained in full, for example because they are clinically the most relevant, are unmodified, with other portions of the data stream being modified. The other portions of the data stream may be modified to greater or lesser extents. For example different portions of the received data stream may be modified such that the ratios of unmodified data volume to modified data volume differ between the different portions which are modified. The amount by which the data is modified, i.e. the ratio of modified to unmodified data volumes, can be selected in dependence on the identified feature.

In some implementations, the identifiable feature comprises, or is determined in dependence on, one or more of the following.

(i) Whether the video data comprises a circle that grows or shrinks.

As the endoscope passes through the port towards the surgical site, the port circumference will appear as a circle in the endoscope video that expands past the screen boundaries. As the endoscope is retracted from the port, the port circumference will appear as a circle in the endoscope video that contracts from beyond the screen boundary. The circle may leave the field of view of the endoscope to one side as the endoscope is moved away from the port. Thus, detecting, for example by image recognition, whether the video image comprises one or other (or both) of an expanding and a contracting circle can enable the detection of whether the endoscope tip passes inwardly or outwardly through the port (or both). Determination of this feature can therefore enable the data modifier to determine whether the endoscope tip is transitioning into or out of the surgical field. Thus this determination can enable the data modifier to generate the modified data accordingly. Data captured before endoscope insertion and/or after endoscope retraction can be modified to reduce its data volume. The data in between these events can be indicated to be of a relatively greater relevance and not to be modified.

(ii) Whether the video data comprises a port-identifying feature.

The port can be marked with a visual indicator that can be detected by an image detection module. On detection of this visual indicator, it can be determined that the endoscope tip has passed through the port. The direction in which the endoscope has passed through the port can be determined based on how the visual indicator moves in the video data and/or on whether the prior state of the endoscope was 'inserted' or 'retracted'.

(iii) A measure of one or more of image white balance, image spectrum, and image gradient from centre to edge of the image, and/or a change in a measure of one or more of image white balance, image spectrum, and image gradient from centre to edge of the image Video data captured from the surgical site is likely to be much redder than video data captured from the operating room. Video data captured from the surgical site is likely to have a greater image gradient from the centre to the edge than video data captured from the operating room. Thus one or more of these measures of the image (or of a series of images) can indicate whether the endoscope is inserted or not. In some cases, a change in the one or more measure, for example between frames in a sequence of video frames, can be used to determine that a transition has occurred. For example, where an earlier frame in a sequence has a lower red content than a later frame in the sequence, it can be determined that a transition from video of the operating room (outside the surgical field) to video of the patient cavity (inside the surgical field) has occurred.

The measure of the image spectrum may comprise a measure obtained within the visible spectrum, outside the visible spectrum, or both inside and outside the visible spectrum. For example the image spectrum may span the visible spectrum. Suitably the image spectrum comprises one or more of infrared and ultraviolet parts of the spectrum. The measure of the image spectrum may comprise a measure obtained across multiple bandwidths, such as two or more of a visible bandwidth, an ultraviolet bandwidth and an infrared bandwidth. In some cases, where there is a drop in the level of UV light between frames, it can be determined that a transition from the operating room (where there may be more/brighter UV sources) to the patient cavity has occurred. An increase in the level of IR light between frames may similarly indicate that a transition from operating room to patient cavity (where there may be relatively higher IR emission) has occurred.

The frames may be successive frames in the sequence, or they may be spaced apart by one or more other frames. A rough determination of the transition into the surgical field or out of the surgical field can be found by comparing frames that are spaced from one another temporally by, say, 30 seconds. Any other suitable time period can be used, as would be apparent to the skilled person. Once a transition occurring in a specified time period has been identified, then frames separated by a smaller time period can be compared. In some cases, frames can be compared at a series of successively smaller time separations. For example, 30 seconds, then 10 seconds, then 2 seconds, then 0.5 seconds. Greater and/or smaller time separation values can be used. More or fewer different time separations can be used. In this way, a finer determination can be iteratively achieved at lower processing cost and/or time.

The measure may comprise that a growing proportion of the image includes one or more of relatively redder light, relatively less UV light, relatively more IR light, and so on. This can indicate that the endoscope is approaching a port or patient cavity. In this way, the measure can be an indication that the captured video is transitioning from being outside the surgical field to being inside the surgical field. The converse may also be true: where the measure comprises that a shrinking proportion of the image includes one or more of relatively redder light, relatively less UV light, relatively more IR light, and so on, it can be determined that the endoscope is transitioning from being inside the surgical field to being outside the surgical field.

The measure may comprise a measure of the absorption of electromagnetic radiation in a given frequency band or bands. For example, a measure of the absorption, such as a differential absorption, can be used to detect patient tissue. This can indicate that the endoscope is within the patient cavity, or perhaps that the patient is visible in the field of view. The measure can be used with a different metric, such as a state of the system, to identify the tissue being viewed (optionally including whether the identified tissue is internal or external).

The measure of the image white balance, image spectrum and/or image gradient may comprise an average value for the image.

(iv) Whether the video data comprises an anatomical feature.

The video data can be analysed to determine objects shown within the video data. Where, for example, internal anatomy such as a blood vessel or internal organ is detected, the system can determine that the endoscope is inside the surgical field. The data modifier can selectively modify parts of the video data that are not defined as being captured within the surgical field. Thus, where a video segment comprises an image of an internal organ, the video segment can be marked as more likely to be relevant to the procedure and so not to be modified. A further check may be made to ensure that the organ identified is indeed internal to the patient at the time, for example by also considering a measure of the image spectrum.

An anatomical feature may be detected that is indicative of the endoscope being outside the surgical field. For example, an analysis of the video data may determine that the video data comprises an external view of a patient's abdomen, or arm. In such cases, the relevant portion of the video data may be marked as being of relatively less relevance to the surgical procedure (for example where the abdomen occupies the whole field of view).

(v) Whether the video data comprises an object known to be external to the surgical field.

Where video data analysis determines that an object in the operating room (such as an operating table, a robotic arm, a heart-rate monitor and so on) is visible, it can be determined that the endoscope is outside the surgical field and is capturing video from the operating room itself. Such a portion of the video data may be marked for modification. The video data can be marked for modification where a known object (e.g. legs of an operating table) occupies at least a portion of the whole field of view.

(vi) The procedure being performed.

For different procedures, the video forming the video data is likely to comprise different characteristics. For instance, the number of times in the procedure that the endoscope is inserted/removed from the port, the duration of the periods of insertion, the surgical site visible during inserted periods, and so on. Basing the identification of the feature on the procedure being performed can enable video analysis of the video data to know what to expect, or roughly what to expect. This, in turn, can enable detection or identification of features in the video with a higher accuracy.

(vii) A machine learning system that has been trained using one or more known features.

An operator can indicate to the system when a feature is present in the data stream, and this indication can be passed to a machine learning system that can learn from the input indication so as to be able to recognise the same or similar features in other data. The machine learning system may comprise a convolutional neural network. The machine learning system may comprise a recurrent neural network.

The identifiable feature may, in some cases, comprise a marker associated with a portion of the data stream. The marker may form part of the data stream, for example the marker may have been added to the data stream during the procedure or at some point afterwards. One or more data channel of the data stream may comprise the marker. For example, the video data can comprise the marker. The marker may take any suitable form, which may be dependent on the data channel with which the marker is associated or of which the marker forms a part. In some cases, the marker may be an augmentation added to the video stream. The augmentation may be added as the video is captured or at some point after the video is captured. The marker can indicate the presence of one or more other feature described herein (such as the stage in a procedure, the visibility of an internal organ, the state of the system and so on). The marker can indicate a state or transition towards, away from or between other such features described herein (such as whether the video is captured inside a surgical field, outside a surgical field, and so on).

Combinations of these features may usefully be used. For example, detecting that a circle expands in the image, followed by an increase in the redness of the image, can be used to determine that the endoscope tip has been inserted through the port. Combinations of features may advantageously increase the accuracy with which such determinations can be made.

Figure 4:
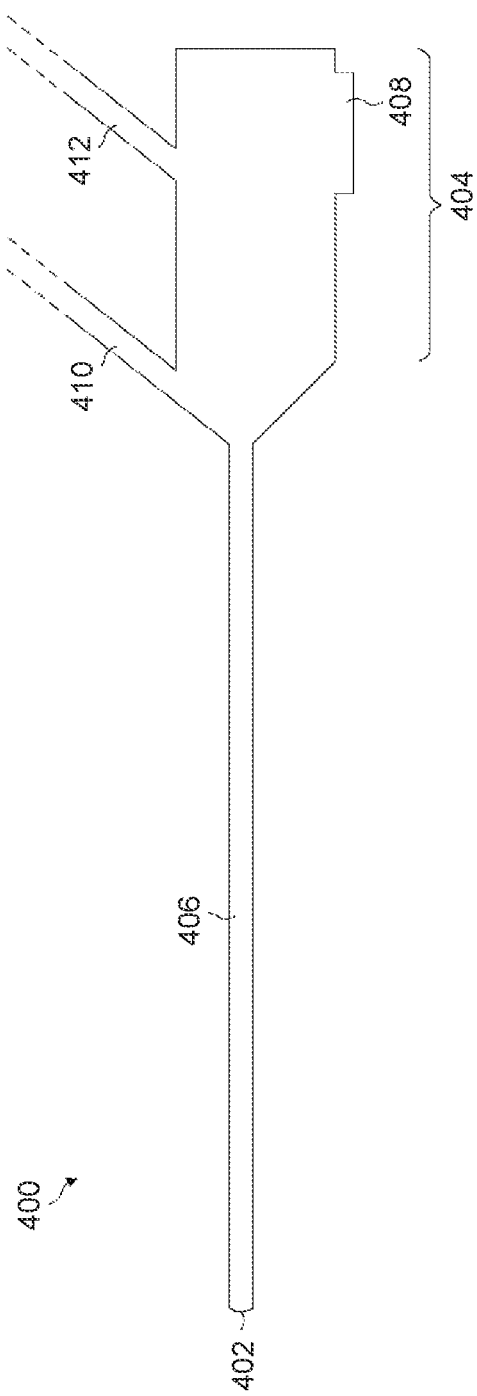
FIG. 4 schematically illustrates an example endoscope that is attachable to a surgical robot arm.

An example endoscope has been described above with respect to FIG. 4. Other types of endoscope can be used with the present techniques. Such endoscopes includes a "chip-on-tip" type endoscope, where the endoscope can be considered to be a probe at the end of which a camera can be mounted. The camera may take the form of a chip, for example a CCD chip, and optionally some associated processing logic (at least some processing logic may be provided separately). The endoscope described with reference to FIG. 4 operates with an external light source. It is also possible to use endoscopes that operate with an internal light source. For example, a light source might be provided as part of the endoscope itself, and light routed to a desired light output location. The light routing can be achieved by one or more fibre optic cable. In some cases, a light source can be provided at or adjacent a tip of the endoscope. Such a light source may comprise an LED. Multiple LEDs can be provided. The light source, whether internal, external, or some combination of internal and external can be controlled so as to vary the intensity of light output and/or the frequency of light output.

In some cases, the endoscope can be provided with a light source (or more generally an illumination source) configured to output light (or more generally, electromagnetic radiation) outside the visible range. Suitably the illumination source is configured to output electromagnetic radiation across a spectrum. The spectrum may comprise one or more of visible light, ultraviolet light and infrared light.

Modifying the data can comprise removing a time slice from the data stream, or blurring/masking at least a portion of the data stream. Suitably modifying the data comprises reducing the quality or fidelity of at least a portion of the data. Suitably the modification of the data is performed on all the data channels, though it need not be. The modification of the data can be performed on all the data channels at once, though it need not be. In some cases, the data modifier can be configured to modify a subset of the data channels. For instance, the data modifier can modify the video data channel, and possibly also the audio data channel, but need not modify the telematics data and/or the state data. Where the data modifier is configured to modify the data channels separately, the data volume modification system is suitably configured to combine the modified data channel(s) with any remaining data channel(s) into the modified data stream before saving or transferring the modified data stream. In some cases, the data channels may be saved and/or transferred separately, or in a group comprising a subset of the data channels.

In some cases, as discussed above, the data modifier can modify a period of the received data stream (chronologically) before a detected or identified feature, for example a first data portion of the received data stream before the identified feature. The data modifier can modify a period of the received data stream (chronologically) after a detected feature, for example a second data portion of the received data stream after the identified feature. One or both of the first data portion and the second data portion can relate to predetermined time periods.

The first data portion can suitably be the portion of the received data stream from the start of the received data stream up to the point of the received data stream at which the feature is identified. The first data portion may instead relate to a given time period, such as 30 seconds, 1 minute, 2 minutes, 5 minutes, 10 minutes and so on. Where the given time period is equal to or greater than the total time from the start of the received data stream up to the point at which the feature is identified, the first data portion comprises the portion of the received data stream from the start to the point of the identified feature. The given time period may end at the time at which the identified feature occurs. That is, the first time period may be a time period ending with the occurrence of the identified feature. The given time period may be selectable, for example by a user. The given time period may be selected automatically. The given time period may be selectable in dependence on the identified feature and/or on the procedure being performed. For example, for a first identified feature, the given time period may be 1 minute and for a second identified feature, the given time period may be 2 minutes or from the start of the received data stream up to the time of the identified feature occurring.

The second data portion can suitably be the portion of the received data stream from the point in the received data stream at which the feature is identified up to the end of the received data stream. The second data portion may instead relate to a further given time period, such as 30 seconds, 1 minute, 2 minutes, 5 minutes, 10 minutes and so on. Where the further given time period is equal to or greater than the total time from the point at which the feature is identified to the end of the received data stream, the second data portion comprises the portion of the received data stream from the identified feature to the end of the received data stream. The further given time period may start at the time at which the identified feature occurs. That is, the second time period may be a time period starting with the occurrence of the identified feature. The further given time period may be selectable, for example by a user. The further given time period may be selected automatically. The further given time period may be selectable in dependence on the identified feature and/or on the procedure being performed. For example, for a third identified feature, the further given time period may be 1 minute and for a fourth identified feature, the further given time period may be 2 minutes or from the time of the identified feature occurring up to the end of the received data stream.

The first time period and the second time period can be the same, but need not be. The first time period and the second time period may be related to one another. For example, the first time period may be one half, one tenth, and so on, of the second time period. Thus, in one example, the first time period is 1 minute and the second time period is 2 minutes. In another example, the first time period is 1 minute and the second time period is 10 minutes. Other ratios between the first time period and the second time period are possible, and may be selected, for example automatically, by a user, in dependence on the identified feature, the procedure being performed, and so on. The first time period may be longer than the second time period.

The data modifier can modify a period of the received data stream (chronologically) between detected features. In some cases, the data modifier can be configured to modify the received data stream for a time period located about (i.e. to either side of) the detected feature.

The data modifying can be configured to identify a further feature in the received data stream indicative of a further event in the surgical procedure, and to generate the modified data stream by modifying a third time period of the received data stream between the identified feature and the identified further feature; or before the first of the identified feature and the identified further feature and after the second of the identified feature and the identified further feature.

Where the third time period is between the identified feature and the identified further feature, the third time period need not be strictly restricted to the time in between the occurrence of the identified feature and the identified further feature. In some examples, the third time period can be longer than the time between the occurrence of the identified feature and the further identified feature. For example, the third time period can additionally cover a time before the first of the identified feature and the further identified feature and/or a time after the second of the identified feature and the further identified feature.

Identifying the feature can comprise determining whether a rule of a set of rules is satisfied and identifying the feature where the rule is satisfied. The rule can be satisfied where a parameter of a group of parameters of the surgical robotic system and/or the surgical procedure matches a predefined criterion. The received data stream can comprise the parameter. The parameter can be determined from analysis of the received data stream.

Suitably the parameter (or more than one parameter of the group of parameters) can be represented in metadata of the received data stream. For example, the metadata can comprise the parameters. Analysis of the received data stream to determine the parameters can comprise determining the metadata of the received data stream and extracting a parameter value from the metadata. Analysis of the received data stream to determine the parameters can comprise image analysis of a video channel, or of a portion of the video channel, of the received data stream. The analysis can comprise image recognition/image matching so as to identify the parameter in the video. Analysis of the received data stream to determine the parameters can comprise analysing a telemetry data portion of the received data stream.

The criterion (or criteria) suitably comprises one or more of the type of instrument, the attachment state of the instrument, the operative state of the surgical robotic system, a characteristic of at least an aspect or portion of the received data stream, and a combination of the above. E.g., the criterion can comprise the instrument being a grasper instrument that is attached to the system and that the system is in a 'surgical mode' indicating that the instrument is under operable control of the surgeon. Where the parameters indicate that this criterion is satisfied, the rule can be met and the feature identified.

The criteria used to identify the feature are suitably selected in dependence on an intended use of the modified data stream and/or on an intended destination for the modified data stream. For example, when the data is to be used for a teaching session on suturing, features used to modify the data stream can include the attachment and detachment of a suturing instrument, and control of the instruments that is indicative of a suturing operation.

As introduced above, it is possible for the data volume of a particular channel to increase whilst reducing the overall data volume. An example of this will now be discussed. Where a received data stream comprises two channels, it is possible to combine a subset of the data from both of those channels into a single channel. The resulting single channel is likely to have a greater data volume than either one of the received channels (though it need not; each channel may be modified as described herein before the channels are combined). However, where the resulting single channel has a data volume that is smaller than the combined data volume of the received channels, a benefit can still be obtained. Data from a first channel can be superimposed on a second channel (or otherwise combined, such as by adding metadata to the second channel). To give an example, joint data of a subset of joints can be superimposed on a video data channel. The resulting video data channel, comprising the superimposed joint data, will have a greater data volume than the received video data channel. The received joint data can then be omitted. Since the omitted joint data has a greater data volume than the subset of joint data, an overall data volume saving is realised.

Figure 7:
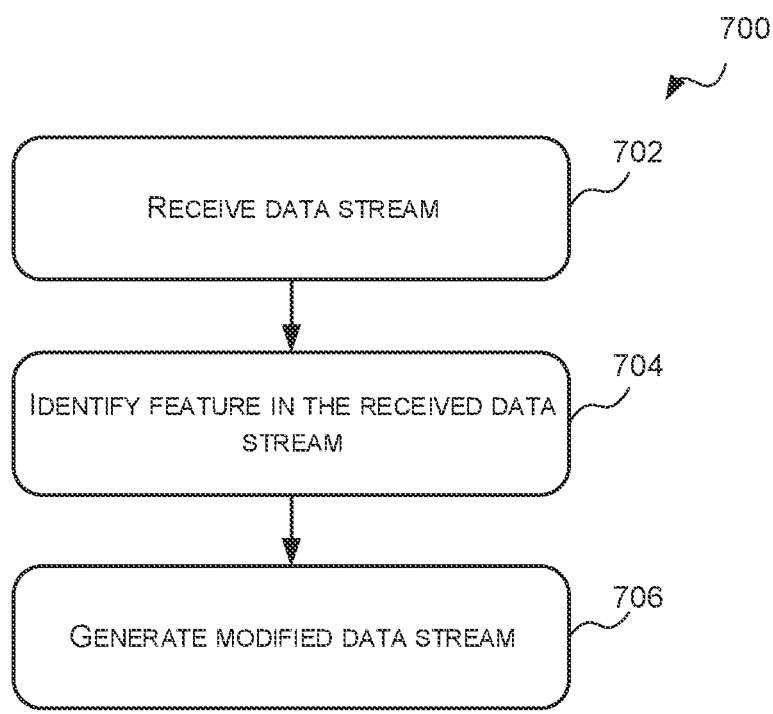
FIG. 7 is a block diagram of an example method of modifying a data stream.

Reference is now made to FIG. 7 which illustrates an example method 700 for automatically generating a modified data stream based on a data stream captured by the surgical robotic system. At block 702, the data stream captured by the system is received. The data stream can be received by the data volume modification system 500 discussed above, for example by the receiver 504. At block 704, a feature in the received data stream is identified. For instance, the feature can comprise a determination of an event or a stage in the procedure, such as that an endoscope has been inserted within a patient cavity. At block 706, a modified data stream is generated. The modified data stream is generated in dependence on the data stream received at block 702 and the feature identified at block 704. The modified data stream is generated so as to reduce the data volume, i.e. such that the modified data stream comprises less data than the received data stream.

In some cases, the video data need not be captured by an endoscope that is attachable to an arm of the surgical robotic system. For example, video data may be captured by an endoscope that is not a robotic endoscope. The endoscope may be a manually controllable endoscope. In this way, the video data, or more generally the data stream, may be captured by a device that is external to (not part of) the surgical robotic system. Such a device is not limited to an endoscope. Such a device may comprise a monitoring device for monitoring a patient and/or the status of a patient. Such a device can comprise one or more of an endoscope, a heart rate monitor, a blood pressure monitor, a blood flow monitor, a breathing monitor and so on.

A data volume modification system may be provided for modifying a data stream captured from a device such as a monitoring device. The data stream may comprise video data. The data volume modification system is suitably configured to receive the data stream, identify a feature of the data stream indicative of an event, and generate, in dependence on the identified feature and the received data stream, a modified data stream with a data volume that is less than the received data stream.

The data volume modification system may comprise a receiver configured to receive the data stream. The data volume modification system may comprise a data modifier configured to generate the modified data stream.

The data modifier may be configured to identify the feature. Identifying the feature may comprise detecting the feature in the received data stream.

The device may comprise an imaging device for imaging inside a surgical field. The device may comprise an imaging device for imaging at a surgical site within a patient. The data stream may comprise data captured from inside the surgical field. The data stream may comprise data captured from the surgical site within the patient. The data stream may comprise video data. The data stream may comprise data captured from outside the surgical field.

The device may be remote from (external to) a surgical robotic system. The data modifier can be for use in or with a surgical robotic system. The data modifier can form part of the surgical robotic system. The data may be captured from the device external to (or remote from) the surgical robotic system and modified at the surgical robotic system. That is, the surgical robotic system (or at least a portion of the surgical robotic system, such as a data volume modification system) may be used to modify data captured remotely from the system. The data captured remotely from the surgical robotic system may be synchronised with data captured by the surgical robotic system. The data captured remotely from the surgical robotic system may be modified in dependence on the data captured by the surgical robotic system.

The feature of the data stream indicative of an event may comprise or be determined in dependence on a feature as described elsewhere herein (full details are not repeated here for brevity). For example, the feature of the data stream may comprise an indication that video data is captured from outside or inside a surgical field, and/or that the video data comprises a transition between being captured from outside a surgical field to/from being captured inside a surgical field. Such a feature may comprise (as described in more detail elsewhere herein) one or more of (including combinations of): whether the video data comprises a circle that grows or shrinks, whether the video data comprises a port-identifying feature, a measure of one or more of image white balance, image spectrum, and image gradient from centre to edge of the image, and/or a change in a measure of one or more of image white balance, image spectrum, and image gradient from centre to edge of the image, whether the video data comprises an anatomical feature, whether the video data comprises an object known to be external to the surgical field, the procedure being performed, and a machine learning system that has been trained using one or more known features.

The data stream may be modified as described elsewhere herein (full details are not repeated here for brevity).

In this way, it is possible to modify data captured remotely from a surgical robotic system, for example using the surgical robotic system. The data captured remotely from the surgical robotic system can be modified before it leaves the operating room. The data captured remotely from the surgical robotic system can be modified at the surgical robotic system, for example as it passes through the surgical robotic system. Further processing of the data captured remotely from the surgical robotic system and/or the modified data can be performed, as described elsewhere herein, including encryption, watermarking, associating with lifespan values and so on.

Figure 8:
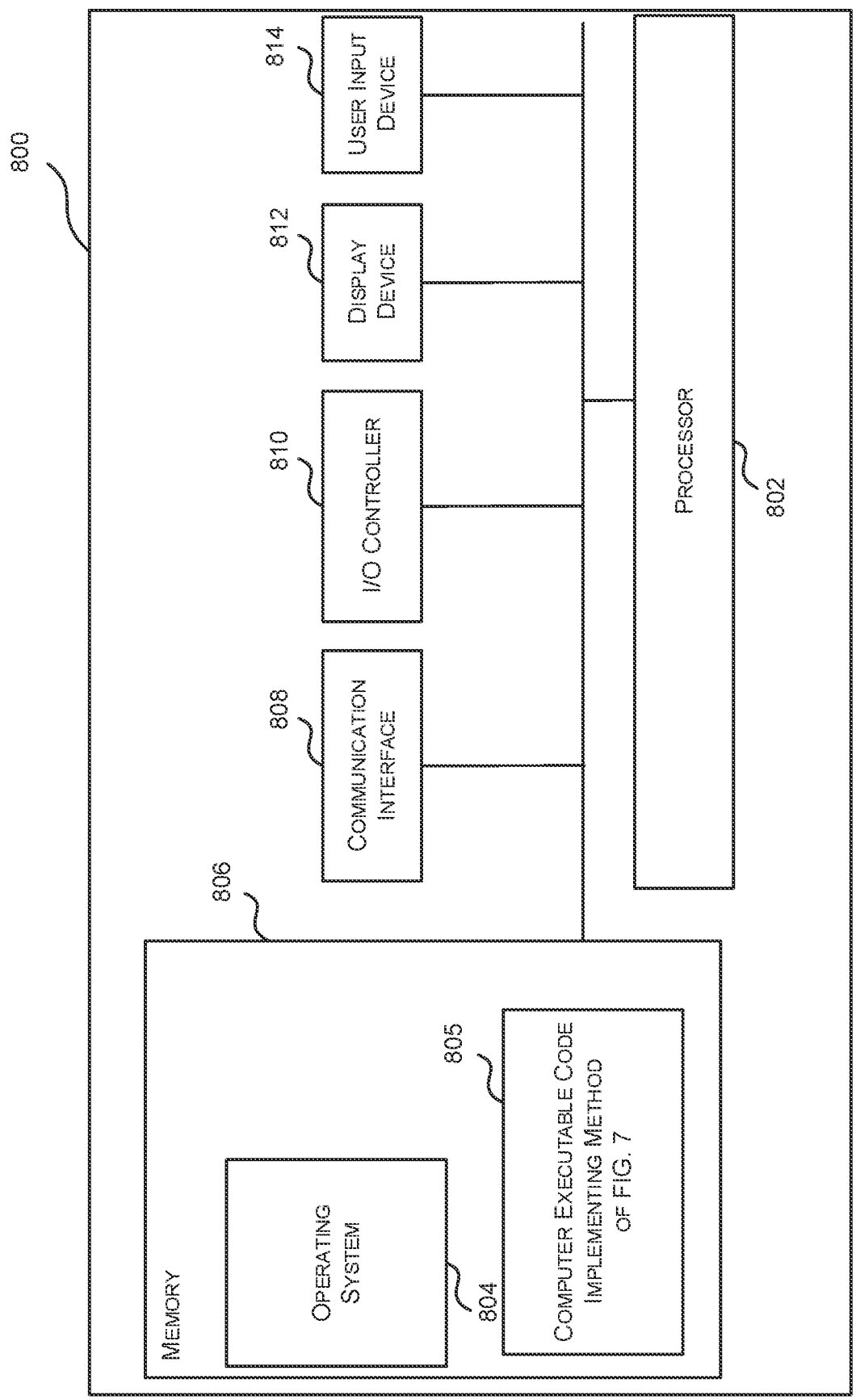
FIG. 8 is a block diagram of an example computing-based device.

Reference is now made to FIG. 8 which illustrates various components of an exemplary computing-based device 800 which may be implemented as any form of a computing and/or electronic device, and in which embodiments of the methods and modification systems described herein may be implemented. The computing-based device 800 comprises one or more processor 802 which may be microprocessors, controllers or any other suitable type of processors for processing computer executable instructions. In some examples, for example where a system on a chip architecture is used, the processors 802 may include one or more fixed function blocks (also referred to as accelerators) which implement a part of the method of modifying a data stream in hardware (rather than software or firmware). Platform software comprising an operating system 804 or any other suitable platform software may be provided at the computing-based device to enable application software, such as software 805 implementing the method of FIG. 7, to be executed on the device.

The computer executable instructions may be provided using any computer-readable media that is accessible by computing-based device 800. Computer-readable media may include, for example, computer storage media such as memory 806 and communications media. Computer storage media (i.e. non-transitory machine-readable media), such as memory 806, includes volatile and non-volatile, removable and non-removable media implemented in any method or technology for storage of information such as computer readable instructions, data structures, program modules or other data. Computer storage media includes, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing-based device. In contrast, communication media may embody computer readable instructions, data structures, program modules, or other data in a modulated data signal, such as a carrier wave, or other transport mechanism. As defined herein, computer storage media does not include communication media. Although the computer storage media (i.e. non-transitory machine-readable media, e.g. memory 806) is shown within the computing-based device 800 it will be appreciated that the storage may be distributed or located remotely and accessed via a network or other communication link (e.g. using communication interface 808).

The computing-based device 800 also comprises an input/output controller 810 arranged to output display information to a display device 812 which may be separate from or integral to the computing-based device 800. The display information may provide a graphical user interface. The input/output controller 810 is also arranged to receive and process input from one or more devices, such as a user input device 814 (e.g. a mouse or a keyboard). This user input may be used to initiate verification. In an embodiment the display device 812 may also act as the user input device 814 if it is a touch sensitive display device. The input/output controller 810 may also output data to devices other than the display device, e.g. a locally connected printing device (not shown).

In the description above actions taken by the system have been split into functional blocks or modules for ease of explanation. In practice, two or more of these blocks could be architecturally combined. The functions could also be split into different functional blocks.

The present techniques have been described in the context of surgical robotic systems, though at least some features described are not limited to such systems, but may be applied to robotic systems more generally. In some examples, the present techniques may be applied to robotic systems that operate remotely. Some examples of situations in which the present techniques may be useful include those that make use of 'snake-like' robots for exploration, investigation or repair. In the case of a surgical robot the end effector could be a surgical tool such as a scissors, surgical cutter, surgical pincer or cauteriser.

Robotic systems can include manufacturing systems, such as vehicle manufacturing systems, parts handling systems, laboratory systems, and manipulators such as for hazardous materials or surgical manipulators.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A method of controlling a data modifier to reduce overall a data volume of a data stream captured by a surgical robotic system, the surgical robotic system comprising a robot having a base and an arm extending from the base to an attachment for an instrument, the arm comprising a plurality of joints whereby the configuration of the arm can be altered, the method comprising:
   receiving a data stream captured by the surgical robotic system, the data stream comprising data relating to a surgical procedure and having a first data volume;
   identifying a feature in the received data stream indicative of an event in the surgical procedure;
   in dependence on the identified feature, determining selected data within the received data stream for which data fidelity is to be retained;
   in dependence on the determined selected data, controlling a data modifier to move between:
      an active state in which the data modifier is arranged to modify the received data stream to generate a modified data stream, and
      an inactive state in which the data modifier is arranged not to modify the received data stream, thereby leaving the received data stream unmodified;
   such that the data modifier selectively modifies in dependence on the identified feature, the received data stream to generate a modified data stream having a second data volume that is smaller than the first data volume whilst retaining the data fidelity of the determined data; and
   outputting the modified data stream.

2. A method according to claim 1, comprising generating the modified data stream by modifying one or more of:
   a first data portion of the received data stream before the identified feature; and
   a second data portion of the received data stream after the identified feature.

3. A method according to claim 2, in which one or both of the first data portion and the second data portion relate to predetermined time periods.

4. A method according to claim 1, comprising identifying a further feature in the received data stream indicative of a further event in the surgical procedure, and generating the modified data stream by modifying a further data portion relating to a further time period of the received data stream:
   between the identified feature and the identified further feature; or
   before the first of the identified feature and the identified further feature and after the second of the identified feature and the identified further feature.

5. A method according to claim 1, in which identifying the feature comprises determining whether a rule of a set of rules is satisfied and identifying the feature where the rule is satisfied.

6. A method according to claim 5, in which the rule is satisfied where a parameter of a group of parameters of the surgical robotic system and/or the surgical procedure matches a predefined criterion.

7. A method according to claim 6, in which the received data stream comprises the parameter or in which the parameter is determined from analysis of the received data stream.

8. A method according to claim 1, in which the received data stream comprises one or more data channel from a group of data channels comprising:
   video data received from an endoscope coupled to the surgical robotic system;
   audio data recorded in respect of the surgical procedure;
   telematics data corresponding to the surgical robotic system;
   state data comprising the state of at least a portion of the surgical robotic system; and
   further data transmitted by additional devices on the local network;
   and in which the method comprises identifying the feature in dependence on one or more data channel from the group of data channels.

9. A method according to claim 8, in which the method comprises identifying the feature in dependence on a first data channel of the group of data channels, and generating the modified data stream comprises modifying one or more of:
   the first data channel and
   a second data channel of the group of data channels.

10. A method according to claim 8, in which the method comprises generating the modified data stream by modifying one or more of:
    a video definition of at least a portion of the video data;
    a number of video channels of at least a portion of the video data;
    a frame rate of at least a portion of the video data;
    a colour gamut of at least a portion of the video data;
    a representation of the state of the robotic system;
    an audio definition of at least a portion of the audio data;
    a number of data channels in the group of data channels.

11. A method according to claim 8, in which the method comprises modifying the received data stream such that the modified data stream comprises one or more of:
    a portion of video data having a first resolution and a portion of video data having a second, lower, resolution;
    a portion of video data having a first number of channels and a portion of video data having a second, smaller, number of channels;

a portion of video data having a first frame rate and a portion of video data having a second, lower, frame rate;

a portion of video data having a first colour gamut and a portion of video data having a second, smaller, colour gamut;

data relating to changes in state of the robotic system in place of data relating to the state of the robotic system at a plurality of points in time between which the state does not change;

a wire frame model of a known shape in the video data in place of full video or graphics render data relating to that known shape;

a description of a structure in the video data in place of full video data relating to that structure; and a description of an absolute location and/or a relative location, and a description of a speed and/or a trajectory of movement, in place of full video data or full telematics data.

12. A method according to claim 11, in which the description of the structure comprises a description of one or more of an anatomical structure, an instrument, and an end effector.

13. A method according to claim 1, in which the identified feature is indicative of a value of or change in one or more of:
   an attachment state of an instrument;
   an operational state of an instrument attached to the arm;
   an operational state or operational mode of the robotic system;
   a configuration of the arm and/or of an instrument attached to the arm; and
   a control state of the control console.

14. A method according to claim 1, in which the identified feature is indicative of one or more of:
   a feature detected in the video data;
   sensor data; and
   data reported by an externally connected system.

15. A method according to claim 1, in which the method comprises generating the modified data stream by compressing at least a portion of one or more data channel from the group of data channels.

16. A method according to claim 1, in which the method comprises generating the modified data stream as the surgical procedure is being performed.

17. A method according to claim 1, in which the method comprises:

generating the modified data stream in real time or substantially real time;

sending the modified data stream to a remote processor thereby enabling the remote processor to perform real time or substantially real time analysis of the modified data stream; and receiving from the remote processor in real time or substantially real time the result of the analysis for assisting an operator of the surgical robotic system.

18. A computer readable-storage medium having stored thereon computer readable instructions that, when executed at a computer system, cause the computer system to perform the method according to claim 1.

19. A data volume modification system for a surgical robotic system for controlling a data modifier to reduce overall a data volume of a data stream in the surgical robotic system, the surgical robotic system comprising a robot having a base and an arm extending from the base to an attachment for an instrument, the arm comprising a plurality of joints whereby the configuration of the arm can be altered, the system comprising:

a receiver configured to receive a data stream captured by the surgical robotic system, the data stream comprising data relating to a surgical procedure and having a first data volume;

a feature detector configured to identify a feature in the received data stream indicative of an event in the surgical procedure;

a data modifier configured to selectively modify the received data stream to generate a modified data stream; and an output configured to output the modified data stream;

wherein the system is configured to, in dependence on the identified feature, determine selected data within the received data stream for which data fidelity is to be retained and, in dependence on the determined selected data, to control the data modifier to move between:

an active state in which the data modifier is arranged to modify the received data stream to generate the modified data stream, where the modified data stream has a second data volume that is smaller than the first data volume whilst retaining the data fidelity of the determined data, and an inactive state in which the data modifier is arranged not to modify the received data stream, thereby leaving the received data stream unmodified.

* * * * *